(12) United States Patent
Weiner et al.

(10) Patent No.: US 6,812,205 B2
(45) Date of Patent: Nov. 2, 2004

(54) SUPPRESSION OF VASCULAR DISORDERS BY MUCOSAL ADMINISTRATION OF HEAT SHOCK PROTEIN PEPTIDES

(75) Inventors: Howard L. Weiner, Brookline, MA (US); Ruth Maron, Brookline, MA (US); Peter Libby, Boston, MA (US)

(73) Assignee: The Brigham & Women's Hospital, Inc., Boston, MA (US)

( * ) Notice: Subject to any disclaimer, the term of this patent is extended or adjusted under 35 U.S.C. 154(b) by 400 days.

(21) Appl. No.: 09/809,745

(22) Filed: Mar. 15, 2001

(65) Prior Publication Data

US 2004/0192592 A1 Sep. 30, 2004

Related U.S. Application Data

(60) Provisional application No. 60/189,855, filed on Mar. 15, 2000.

(51) Int. Cl.[7] .......................... A61K 38/00; C07K 14/00
(52) U.S. Cl. ........................ 514/2; 530/350; 530/300; 435/7.1; 424/93.21; 424/40
(58) Field of Search ............................. 514/2; 530/350; 530/300; 435/7.1; 424/93.21, 409.1, 40

(56) References Cited

U.S. PATENT DOCUMENTS

| | | |
|---|---|---|
| 3,561,444 A | 2/1971 | Boucher |
| 3,699,963 A | 10/1972 | Zaffaroni |
| 3,703,173 A | 11/1972 | Dixon |
| 3,944,064 A | 3/1976 | Bashaw et al. |
| 3,948,262 A | 4/1976 | Zaffaroni |
| 3,993,073 A | 11/1976 | Zaffaroni |
| 4,226,848 A | 10/1980 | Nagai et al. |
| 4,309,404 A | 1/1982 | DeNeale et al. |
| 4,309,406 A | 1/1982 | Guley et al. |
| 4,556,552 A | 12/1985 | Porter et al. |
| 4,624,251 A | 11/1986 | Miller |
| 4,635,627 A | 1/1987 | Gam |
| 4,675,189 A | 6/1987 | Kent et al. |
| 4,704,295 A | 11/1987 | Porter et al. |
| 4,713,243 A | 12/1987 | Schiraldi et al. |
| 4,837,027 A | 6/1989 | Lee et al. |
| 4,895,724 A | 1/1990 | Cardinal et al. |
| 4,917,895 A | 4/1990 | Lee et al. |
| 4,940,587 A | 7/1990 | Jenkins et al. |
| 4,985,253 A | 1/1991 | Fujioka et al. |
| 5,110,597 A | 5/1992 | Wong et al. |
| 5,141,750 A | 8/1992 | Lee et al. |
| 5,151,272 A | 9/1992 | Engstrom et al. |
| 5,236,704 A | 8/1993 | Fujioka et al. |
| 5,284,660 A | 2/1994 | Lee et al. |
| 5,354,691 A | 10/1994 | Van Eden et al. |
| 5,356,635 A | 10/1994 | Raman et al. |
| 5,371,109 A | 12/1994 | Engstrom et al. |
| 5,405,619 A | 4/1995 | Santus et al. |
| 5,416,071 A | 5/1995 | Igari et al. |
| 5,578,303 A | * 11/1996 | Cohen et al. ............ 424/93.71 |
| 5,641,474 A | 6/1997 | Hafler et al. |
| 5,840,855 A | 11/1998 | Shinnick et al. |
| 5,856,305 A | 1/1999 | Lucietto et al. |
| 5,869,054 A | 2/1999 | Weiner et al. |
| 5,869,093 A | 2/1999 | Weiner et al. |
| 5,961,977 A | 10/1999 | Hafler et al. |
| 5,993,803 A | * 11/1999 | Cohen et al. ............ 424/93.71 |
| 6,007,821 A | * 12/1999 | Srivastava et al. ....... 424/193.1 |
| 6,475,490 B1 | * 11/2002 | Srivastava et al. ....... 424/193.1 |

FOREIGN PATENT DOCUMENTS

| | | |
|---|---|---|
| EP | 259013 B1 | 6/1991 |
| EP | 354742 B1 | 3/1994 |
| EP | 205282 B1 | 9/1995 |
| EP | 516141 b1 | 8/1996 |
| WO | WO85/02092 A1 | 5/1985 |
| WO | WO88/10120 A1 | 12/1988 |
| WO | WO88/1012 0 A1 | 12/1988 |
| WO | WO91/01333 A1 | 2/1991 |
| WO | WO95/11011 A1 | 4/1995 |
| WO | WO95/15191 A1 | 6/1995 |
| WO | WO95/25744 A  * | 9/1995 |
| WO | WO95/25744 A1 | 9/1995 |
| WO | WO95/27499 A1 | 10/1995 |
| WO | WO95/27500 A1 | 10/1995 |
| WO | WO91/01333 A1 | 2/1997 |
| WO | WO00/20019 A2 | 4/2000 |

OTHER PUBLICATIONS

Padgett, D. A. et al. (2003) How stress influences the immune response. Trends Immunol. vol. 24, pp. 444–448, Review.*

Lloyd, C. E. et al. (1996) Coronary artery disease in IDDM. Gender differences in risk factors but not risk. Arterioscler. Thromb. Vasc. Biol. vol. 16, pp. 720–726.*

(List continued on next page.)

*Primary Examiner*—Karen Cochrane Carlson
*Assistant Examiner*—Samuel Wei Liu
(74) *Attorney, Agent, or Firm*—Wolf, Greenfield & Sacks, P.C.

(57) ABSTRACT

Disclosed herein are methods for treating vascular disorders in mammals. The methods involve administering one or more agents selected from the group consisting of a heat shock protein (HSP), a therapeutically effective fragment and a therapeutically effective analog of a heat shock protein in a form suitable for mucosal administration. In some embodiments the heat shock protein of the method is mycobacterial HSP65. In some embodiments the heat shock protein is human HSP60. In some embodiments the heat shock protein is chlamydial HSP60. The method is of particular value in the treatment of atherosclerosis. Also disclosed are compositions useful for treating vascular disorders in mammals. The compositions include one or more agents selected from the group consisting of heat shock protein, therapeutically effective fragments and therapeutically effective analogs of said heat shock protein in aerosol or oral form. In some embodiments the heat shock protein of the composition is mycobacterial HSP65. In some embodiments the heat shock protein of the method is human HSP60. In some embodiments the heat shock protein is chlamydial HSP60. The composition is of particular value in the treatment of atherosclerosis.

13 Claims, 6 Drawing Sheets

OTHER PUBLICATIONS

Shi, C. et al. (1996) Immunologic basis of transplant–associated arteriosclerosis. Proc. Natl. Acad. Sci. U S A. vol. 93, pp. 4051–4056.*

Kol, A. et al. (Jan. 2000) Cutting edge: heat shock protein (HSP) 60 activates the innate immune response: CD14 is an essential receptor for HSP60 activation of mononuclear cells. J. Immunol. vol. 164, pp. 13–17.*

Kim, K. K. et al. (1998) Crystal structure of a small heat–shock protein, Nature, vol. 394, pp. 595–599.*

Sumanasekera, W. K. et al. (2003) Heat Shock Protein–90 (Hsp90) Acts as a Repressor of Peroxisome Proliferator–Activated Receptor–alpha (PPARalpha) and PPARbeta Activity. Biochemistry, vol. 42, pp. 10726–10735.*

Schiene–Fischer, C. et al. (2002) The hsp 70 chaperone DnaK is a secondary amide peptide bond cis–trans isomerase. Nat. Struct. Biol. vol. 9, pp. 419–424.*

Wick, G. (1999) Autoimmunity and atherosclerosis. Am. Heart J. vol. 138, pp. S444–9. Review.*

Chen W. et al., Human 60–kDa heat–shock protein: a danger signal to the innate immune system. J. Immunol. Mar. 15, 1999;162(6):3212–9.*

Francis JN et al., The route of administration of an immunodominant peptide derived from heat–shock protein 65 dramatically affects disease outcome in pristane–induced arthritis. Immunology. Mar. 2000;99(3):338–44.*

Haque MA et al., Suppression of adjuvant arthritis in rats by induction of oral tolerance to mycobacterial 65–kDa heat shock protein. Eur J Immunol. Nov. 1996;26(11):2650–6.*

Prakken BJ et al., Peptide–induced nasal tolerance for a mycobacterial heat shock protein 60 T cell epitope in rats suppresses both adjuvant arthritis and nonmicrobially induced experimental arthritis. Proc Natl Acad Sci U S A. Apr. 1997;94(7):3284–9.*

Thompson SJ et al., An immunodominant epitope from mycobacterial 65–kDa heat shock protein protects against pristane–induced arthritis. J Immunol. May 1, 1998;160(9):4628–34.*

Van Der Zee R et al., T cell responses to conserved bacterial heat–shock protein epitopes induce resistance in experimental autoimmunity. Semin Immunol. Feb. 1998;10(1):35–41.*

Van Eden W et al., Heat–shock protein T–cell epitopes trigger a spreading regulatory control in a diversified arthritogenic T–cell response. Immunol Rev. Aug. 1998;164:169–74.*

Berberian PA et al., Immunohistochemical localization of heat shock protein–70 in normal–appearing and atherosclerotic specimens of human arteries. Am J Pathol. Jan. 1990; 136(1):71–80.

Johnson AD et al., Atherosclerosis alters the localization of HSP70 in human and macaque aortas. Exp Mol Pathol. Jun. 1993;58(3):155–68.

Johnson AD et al., Differential distribution of 70–kD heat shock protein in atherosclerosis. Its potential role in arterial SMC survival. Arteriocsler Thromb Vasc Biol. Jan. 1995; 15(1):27–36.

Johnson AD et al., Effect of heat shock proteins on survival of isolated aortic cells from normal and atherosclerotic cynomolgus macaques. Atherosclerosis. Oct. 1990; 84(2–3): 111–9.

Afek A et al., Immunization of low–density lipoprotein receptor deficient (LDL–RD) mice with heat shock protein 65 (HSP–65) promotes early atherosclerosis. J. Autoimmun. Mar. 2000;14(2):115–21.

Dahiyat BI et al., Denovo protein design; fully automated sequence selection. Science. Oct. 3, 1997;278(5335):82–7.

George J et al., Enhanced fatty streak formation in C57BL/6J mice by immunization with heat shock protein–65. Arterioscler Thromb Vasc Biol. Mar. 1999; 19(3):505–10.

George J et al., Requisite role for interleukin–4 in the acceleration of fatty streaks induced by heat shock protein 65 or Mycobacterium tuberculosis. Circ Res. Jun. 23, 2000;86(12):1203–10.

Hunter et al., The gastric emptying of hard gelatin capsules. Int J Pharmaceutics. 1983; 17:59–64.

Jindal S et al., Primary structure of a human mitochondrial protein homologous to the bacterial and plant chaperonins and to the 65–kilodalton mycobacterial antigen. Mol Cell Biol. May 1989;9(5):2279–83.

Kalman S et al., Comparative genomes of Chlamydia pneumoniae and C. trachomatis. Nat. Genet. Apr. 1999;21(4):385–9.

Kaufmann SH, Heat shock proteins and the immune response. Immunol Today. Apr. 1990;11(4):129–36.

Keren P et al., Effect of hyperglycemia and hyperlipidemia on atherosclerosis in LDL receptor–deficient mice: establishment of a combined model and association with the heat shock protein 65 immunity. Diabetes. Jun. 2000;49(6):1064–9.

Kikuta LC et al. Isolation and sequence analysis of the Chlamydia pneumoniae GroE operon. Infect. Immun. Dec. 1991;59(12):4665–9.

Kol A et al., Chlamydial and human heat shock protein 60s activate human vascular endothelium, smooth muscle cells, and macrophages. J Clin Invest. Feb. 1999;103(4):571–7.

Kol A et al. Chlamydial heat shock protein 60 localizes in human atherons and regulates macrophage tumor necrosis factor–alpha and matrix metalloproteinase expression. Circulation. Jul. 28, 1998;98(4):300–7.

Kol A et al., Cutting edge: heat shock protein (HSP) 60 activates the innate immune response: CDI4 is an essential receptor for HSP 60 activation of mononuclear cells. J Immunol. Jan. 1, 2000;164(1):13–7.

Lindquist S, The heat–shock response. Annu Rev Biochem. 1986;55:1151–91.

Mach F et al., Reduction of atherosclerosis in mice by inhibition of CD40 signalling. Nature. Jul. 9, 1998;394(6689):200–3.

Maron R. et al., Mucosal administration of HSP 65 decreases atherosclerosis and inflammation in the aortic arch of LDL receptor deficient mice. AAI/CIS Joint Annual Meeting, Seattle, WA, May 12–16, 2000; FASEB J. Apr. 20, 2000; 14(6):A1199. (Abstract No. 183.9).

Merrifield RB, Peptide synthesis on a solid polymer. Fed Proc Am Soc Exp Biol. 1962;21:412 (Abstract).

Merrifield RB, Solid phase peptide synthesis. I. The synthesis of tetrapeptide. J Am Chem Soc. Jul. 20, 1963; 85:2149–54.

Metzler B et al., Inhibition of arteriosclerosis by T–cell depletion in normocholesterolemic rabbits immunized with heat shock protein 65. Arterioscler Thromb Vasc Biol. Aug. 1999;19(8): 1905–11.

Mitchell AR et al., tert–Butoxycarbonylaminoacyl–4–(oxymethyl)–phenylacetamidomethyl–resin, a more acid–resistant support for solid–phase peptide synthesis. J Am Chem Soc. Nov. 10, 1976;98(23):7357–62.

Morimoto RI, Heat shock: the role of transient inducible responses in cell damage, transformation, and differentiation. *Cancer Cells.* Aug. 1991; 3(8):295–301.

Nicoletti A et al., Immunomodulation of atherosclerosis: myth and reality. *J Intern Med.* Mar. 2000;247(3):397–405.

Nover L, HSFs and HSPs—a stressful program on transcription factors and chaperones. Stress Proteins and the Heat Shock Response, sponsored by Cold Spring Harbor Laboratory, Cold Spring Harbor, NY USA, Apr. 29–May 2, 1991. *New Biol.* Sep. 1991;3(9):855–9.

Pelham HR, Heat shock and the sorting of luminal ER proteins. *EMBO J.* Nov. 1989;8(11):3171–6.

Pelham HR, Speculations on the functions of the major heat shock and glucose–regulated proteins. *Cell.* Sep. 26, 1986;46(7):959–61.

Qiao JH et al., Pathology of atheromatous lesions in inbred and genetically engineered mice. Genetic determination of arterial calcification. *Arterioscler Thromb.* Sep. 1994;14(9):1480–7.

Shinnick TM, The 65–kilodalton antigen of *Mycobacterium tuberculosis*. *J Bacteriol.* Mar. 1987;169(3):1080–8.

Shoenfeld Y et al., Atherosclerosis as an infection, inflammatory and autoimmune disease. Trends Immunol. Jun. 2001;22(6):293–5.

Shoenfeld Y et al., Heat shock protein 60/65, beta 2–glycoprotein I and oxidized LDL as players in murine atherosclerosis. *J. Autoimmun.* Sep. 2000; 15(2):199–202.

Smart JD et al., An in–vitro investigation of mucosa–adhesive materials for use in controlled drug delivery. *J Pharm Pharmacol.* May 1984;36(5):295–9.

Thole JE et al., Characterization, sequence determination, and immunogenicity of a 64–kilodalton protein of *Mycobacterium bovia* BCG expressed in *Escherichia coli* K–12. *Infect Immun.* Jun. 1987;55(6):1466–75.

Wick G et al., Role of heat shock protein 65/60 in the pathogenesis of atherosclerosis. *Int Arch Allergy Immunol.* May–Jun. 1995;107(1–3):130–1.

Xu Q et al., Increased expression of heat shock protein 65 coincides with a population of infiltrating T lymphocytes in atherosclerotic lesions of rabbits specifically responding to heat shock protein 65. *J Clin Invest.* Jun. 1993;91(6):2693–702.

Xu Q et al., Induction of arteriosclerosis in normocholesterolemic rabbits by immunization with heat shock protein 65. *Arterioscler Thromb.* Jul. 1992; 12(7):789–99.

Xu Q et al., Regression of arteriosclerotic lesions induced by immunization with heat shock protein 65–containing material in normocholesterolemic, but not hypercholesterolemic, rabbits. *Atherosclerosis.* Jun. 1996;123(1–2):145–55.

Yuan Y et al., Monoclonal antibodies define genus–specific, species–specific, and cross–reactive epitopes of the chlamydial 60–kilodalton heat shock protein (hsp60): specific immunodetection and purification of chlamydial hsp60. *Infect Immun.* Jun. 1992;60(6):2288–96.

* cited by examiner

FIGURE 2
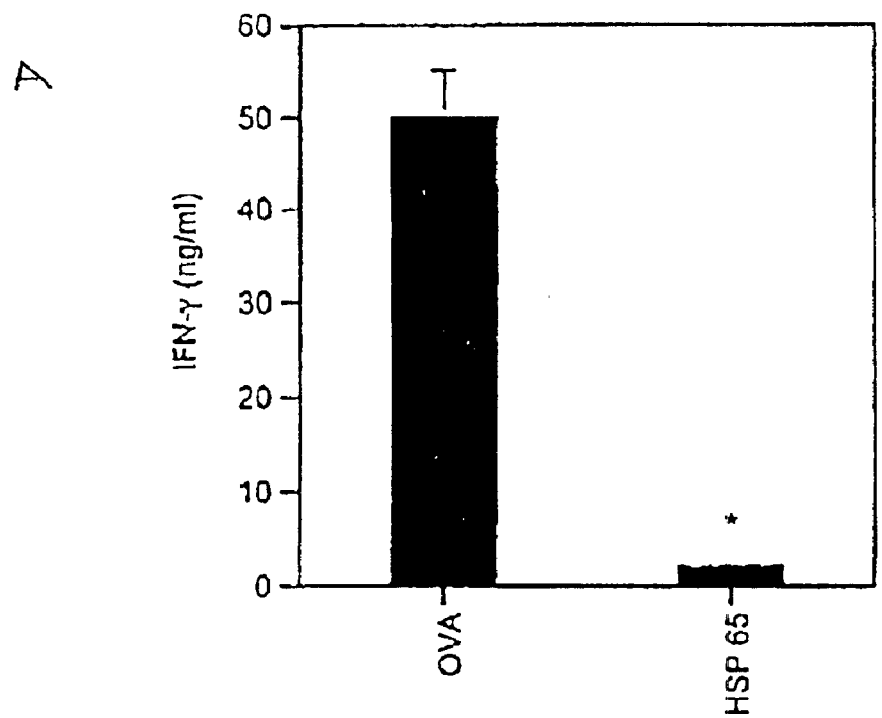
A
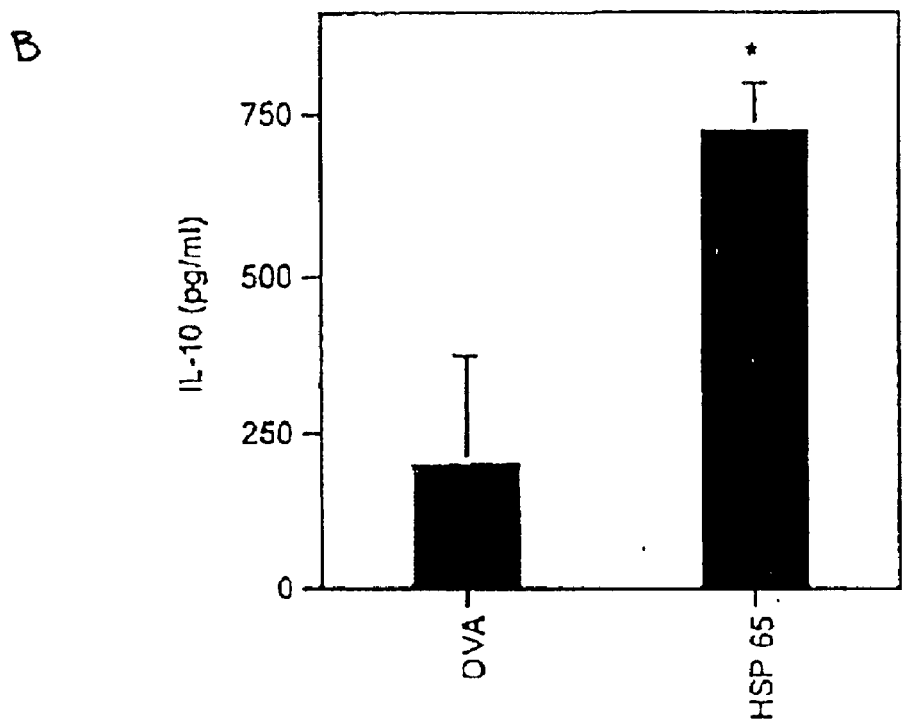
B

SEQUENCE LISTING

<160> NUMBER OF SEQ ID NOS: 3

<210> SEQ ID NO 1
<211> LENGTH: 540
<212> TYPE: PRT
<213> ORGANISM: M. tuberculosis

<400> SEQUENCE: 1

```
Met Ala Lys Thr Ile Ala Tyr Asp Glu Glu Ala Arg Arg Gly Leu Glu
1               5                   10                  15

Arg Gly Leu Asn Ala Leu Ala Asp Ala Val Lys Val Thr Leu Gly Pro
            20                  25                  30

Lys Gly Arg Asn Val Val Leu Glu Lys Lys Trp Gly Ala Pro Thr Ile
        35                  40                  45

Thr Asn Asp Gly Val Ser Ile Ala Lys Glu Ile Glu Leu Glu Asp Pro
    50                  55                  60

Tyr Glu Lys Ile Gly Ala Glu Leu Val Lys Glu Val Ala Lys Lys Thr
65                  70                  75                  80

Asp Asp Val Ala Gly Asp Gly Thr Thr Thr Ala Thr Val Leu Ala Gln
                85                  90                  95

Ala Leu Val Arg Glu Gly Leu Arg Asn Val Ala Ala Gly Ala Asn Pro
            100                 105                 110

Leu Gly Leu Lys Arg Gly Ile Glu Lys Ala Val Glu Lys Val Thr Glu
        115                 120                 125

Thr Leu Leu Lys Gly Ala Lys Glu Val Glu Thr Lys Glu Gln Ile Ala
    130                 135                 140

Ala Thr Ala Ala Ile Ser Ala Gly Asp Gln Ser Ile Gly Asp Leu Ile
145                 150                 155                 160

Ala Glu Ala Met Asp Lys Val Gly Asn Glu Gly Val Ile Thr Val Glu
                165                 170                 175
```

-continued

```
Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Pro Glu Arg
        195                 200                 205

Gln Glu Ala Val Leu Glu Asp Pro Tyr Ile Leu Val Ser Ser Lys
    210                 215                 220

Val Ser Thr Val Lys Asp Leu Leu Pro Leu Glu Lys Val Ile Gly
225                 230                 235                 240

Ala Gly Lys Pro Leu Leu Ile Ile Ala Glu Asp Val Glu Gly Glu Ala
                245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
        275                 280                 285

Asp Met Ala Ile Leu Thr Gly Gly Gln Val Ile Ser Glu Glu Val Gly
    290                 295                 300

Leu Thr Leu Glu Asn Ala Asp Leu Ser Leu Leu Gly Lys Ala Arg Lys
305                 310                 315                 320

Val Val Val Thr Lys Asp Glu Thr Thr Ile Val Glu Gly Ala Gly Asp
                325                 330                 335

Thr Asp Ala Ile Ala Gly Arg Val Ala Gln Ile Arg Gln Glu Ile Glu
            340                 345                 350

Asn Ser Asp Ser Asp Tyr Asp Arg Glu Lys Leu Gln Glu Arg Leu Ala
        355                 360                 365

Lys Leu Ala Gly Gly Val Ala Val Ile Lys Ala Gly Ala Ala Thr Glu
    370                 375                 380

Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Val Thr
                405                 410                 415

Leu Leu Gln Ala Ala Pro Thr Leu Asp Glu Leu Lys Leu Glu Gly Asp
            420                 425                 430

Glu Ala Thr Gly Ala Asn Ile Val Lys Val Ala Leu Glu Ala Pro Leu
        435                 440                 445

Lys Gln Ile Ala Phe Asn Ser Gly Leu Glu Pro Gly Val Val Ala Glu
    450                 455                 460

Lys Val Arg Asn Leu Pro Ala Gly His Gly Leu Asn Ala Gln Thr Gly
465                 470                 475                 480

Val Tyr Glu Asp Leu Leu Ala Ala Gly Val Ala Asp Pro Val Lys Val
                485                 490                 495

Thr Arg Ser Ala Leu Gln Asn Ala Ala Ser Ile Ala Gly Leu Phe Leu
            500                 505                 510

Thr Thr Glu Ala Val Val Ala Asp Lys Pro Glu Lys Glu Lys Ala Ser
        515                 520                 525

Val Pro Gly Gly Gly Asp Met Gly Gly Met Asp Phe
    530                 535                 540

<210> SEQ ID NO 2
<211> LENGTH: 573
<212> TYPE: PRT
<213> ORGANISM: H. sapiens

<400> SEQUENCE: 2

Met Leu Arg Leu Pro Thr Val Phe Arg Gln Met Arg Pro Val Ser Arg
1               5                   10                  15
```

-continued

| | | | | | | | | | | | |
|---|---|---|---|---|---|---|---|---|---|---|---|
|Val|Leu|Ala|Pro|His|Leu|Thr|Arg|Ala|Tyr|Ala|Lys|Asp|Val|Lys|Phe|

Val Leu Ala Pro His Leu Thr Arg Ala Tyr Ala Lys Asp Val Lys Phe
                 20                  25                  30

Gly Ala Asp Ala Arg Ala Leu Met Leu Gln Gly Val Asp Leu Leu Ala
             35                  40                  45

Asp Ala Val Ala Val Thr Met Gly Pro Lys Gly Arg Thr Val Ile Ile
         50                  55                  60

Glu Gln Ser Trp Gly Ser Pro Lys Val Thr Lys Asp Gly Val Thr Val
 65                  70                  75                  80

Ala Lys Ser Ile Asp Leu Lys Asp Lys Tyr Lys Asn Ile Gly Ala Lys
                     85                  90                  95

Leu Val Gln Asp Val Ala Asn Asn Thr Asn Glu Glu Ala Gly Asp Gly
             100                 105                 110

Thr Thr Thr Ala Thr Val Leu Ala Arg Ser Ile Ala Lys Glu Gly Phe
             115                 120                 125

Glu Lys Ile Ser Lys Gly Ala Asn Pro Val Glu Ile Arg Arg Gly Val
             130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                 165                 170                 175

Asn Gly Asp Lys Glu Ile Gly Asn Ile Ile Ser Asp Ala Met Lys Lys
             180                 185                 190

Val Gly Arg Lys Gly Val Ile Thr Val Lys Asp Gly Lys Thr Leu Asn
             195                 200                 205

Asp Glu Leu Glu Ile Ile Glu Gly Met Lys Phe Asp Arg Gly Tyr Ile
         210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                 245                 250                 255

Ile Val Pro Ala Leu Glu Ile Ala Asn Ala His Arg Lys Pro Leu Val
             260                 265                 270

Ile Ile Ala Glu Asp Val Asp Gly Glu Ala Leu Ser Thr Leu Val Leu
         275                 280                 285

Asn Arg Leu Lys Val Gly Leu Gln Val Val Ala Val Lys Ala Pro Gly
         290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                 325                 330                 335

Val Gln Pro His Asp Leu Gly Lys Val Gly Glu Val Ile Val Thr Lys
             340                 345                 350

Asp Asp Ala Met Leu Leu Lys Gly Lys Gly Asp Lys Ala Gln Ile Glu
             355                 360                 365

Lys Arg Ile Gln Glu Ile Ile Glu Gln Leu Asp Val Thr Thr Ser Glu
         370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                 405                 410                 415

Lys Lys Asp Arg Val Thr Asp Ala Leu Asn Ala Thr Arg Ala Ala Val
             420                 425                 430

-continued

```
Glu Glu Gly Ile Val Leu Gly Gly Cys Ala Leu Leu Arg Cys Ile
        435                 440                 445
Pro Ala Leu Asp Ser Leu Thr Pro Ala Asn Glu Asp Gln Lys Ile Gly
450                 455                 460
Ile Glu Ile Ile Lys Arg Thr Leu Lys Ile Pro Ala Met Thr Ile Ala
465                 470                 475                 480
Lys Asn Ala Gly Val Glu Gly Ser Leu Ile Val Glu Lys Ile Met Gln
                485                 490                 495
Ser Ser Ser Glu Val Gly Tyr Asp Ala Met Ala Gly Asp Phe Val Asn
            500                 505                 510
Met Val Glu Lys Gly Ile Ile Asp Pro Thr Lys Val Val Arg Thr Ala
        515                 520                 525
Leu Leu Asp Ala Ala Gly Val Ala Ser Leu Leu Thr Thr Ala Glu Val
    530                 535                 540
Val Val Thr Glu Ile Pro Lys Glu Glu Lys Asp Pro Gly Met Gly Ala
545                 550                 555                 560
Met Gly Gly Met Gly Gly Gly Met Gly Gly Met Phe
                565                 570

<210> SEQ ID NO 3
<211> LENGTH: 544
<212> TYPE: PRT
<213> ORGANISM: C. pneumoniae

<400> SEQUENCE: 3

Met Ala Ala Lys Asn Ile Lys Tyr Asn Glu Glu Ala Arg Lys Lys Ile
1               5                   10                  15
His Lys Gly Val Lys Thr Leu Ala Glu Ala Val Lys Val Thr Leu Gly
                20                  25                  30
Pro Lys Gly Arg His Val Val Ile Asp Lys Ser Phe Gly Ser Pro Gln
            35                  40                  45
Val Thr Lys Asp Gly Val Thr Val Ala Lys Glu Ile Glu Leu Glu Asp
        50                  55                  60
Lys His Glu Asn Met Gly Ala Gln Met Val Lys Glu Val Ala Ser Lys
65                  70                  75                  80
Thr Ala Asp Lys Ala Gly Asp Gly Thr Thr Thr Ala Thr Val Leu Ala
                85                  90                  95
Glu Ala Ile Tyr Ser Glu Gly Leu Arg Asn Val Thr Ala Gly Ala Asn
            100                 105                 110
Pro Met Asp Leu Lys Arg Gly Ile Asp Lys Ala Val Lys Val Val Val
        115                 120                 125
Asp Glu Leu Lys Lys Ile Ser Lys Pro Val Gln His His Lys Glu Ile
    130                 135                 140
Ala Gln Val Ala Thr Ile Ser Ala Asn Asn Asp Ser Glu Ile Gly Asn
145                 150                 155                 160
Leu Ile Ala Glu Ala Met Glu Lys Val Gly Lys Asn Gly Ser Ile Thr
                165                 170                 175
Val Glu Glu Ala Lys Gly Phe Glu Thr Val Leu Asp Val Val Glu Gly
            180                 185                 190
Met Asn Phe Asn Arg Gly Tyr Leu Ser Ser Tyr Phe Ser Thr Asn Pro
        195                 200                 205
Glu Thr Gln Glu Cys Val Leu Glu Asp Ala Leu Ile Leu Ile Tyr Asp
    210                 215                 220
Lys Lys Ile Ser Gly Ile Lys Asp Phe Leu Pro Val Leu Gln Gln Val
225                 230                 235                 240
```

-continued

```
Ala Glu Ser Gly Arg Pro Leu Leu Ile Ile Ala Glu Glu Ile Glu Gly
            245                 250                 255

Glu Ala Leu Ala Thr Leu Val Val Asn Arg Leu Arg Ala Gly Phe Arg
            260                 265                 270

Val Cys Ala Val Lys Ala Pro Gly Phe Gly Asp Arg Arg Lys Ala Met
            275                 280                 285

Leu Glu Asp Ile Ala Ile Leu Thr Gly Gly Gln Leu Val Ser Glu Glu
            290                 295                 300

Leu Gly Met Lys Leu Glu Asn Thr Thr Leu Ala Met Leu Gly Lys Ala
305                 310                 315                 320

Lys Lys Val Ile Val Thr Lys Glu Asp Thr Thr Ile Val Glu Gly Leu
            325                 330                 335

Gly Asn Lys Pro Asp Ile Gln Ala Arg Cys Asp Asn Ile Lys Lys Gln
            340                 345                 350

Ile Glu Asp Ser Thr Ser Asp Tyr Asp Lys Glu Lys Leu Gln Glu Arg
            355                 360                 365

Leu Ala Lys Leu Ser Gly Gly Val Ala Val Ile Arg Val Gly Ala Ala
            370                 375                 380

Thr Glu Ile Glu Met Lys Glu Lys Lys Asp Arg Val Asp Asp Ala Gln
385                 390                 395                 400

His Ala Thr Ile Ala Ala Val Glu Glu Gly Ile Leu Pro Gly Gly Gly
            405                 410                 415

Thr Ala Leu Val Arg Cys Ile Pro Thr Leu Glu Ala Phe Leu Pro Met
            420                 425                 430

Leu Ala Asn Glu Asp Glu Ala Ile Gly Thr Arg Ile Ile Leu Lys Ala
            435                 440                 445

Leu Thr Ala Pro Leu Lys Gln Ile Ala Ser Asn Ala Gly Lys Glu Gly
            450                 455                 460

Ala Ile Ile Cys Gln Gln Val Leu Ala Arg Ser Ala Asn Glu Gly Tyr
465                 470                 475                 480

Asp Ala Leu Arg Asp Ala Tyr Thr Asp Met Ile Asp Ala Gly Ile Leu
            485                 490                 495

Asp Pro Thr Lys Val Thr Arg Ser Ala Leu Glu Ser Ala Ala Ser Ile
            500                 505                 510

Ala Gly Leu Leu Leu Thr Thr Glu Ala Leu Ile Ala Asp Ile Pro Glu
            515                 520                 525

Glu Lys Ser Ser Ser Ala Pro Ala Met Pro Ser Ala Gly Met Asp Tyr
            530                 535                 540
```

SUPPRESSION OF VASCULAR DISORDERS BY MUCOSAL ADMINISTRATION OF HEAT SHOCK PROTEIN PEPTIDES

RELATED APPLICATIONS

This application claims priority to U.S. Provisional Patent Application No. 60/189,855, filed Mar. 15, 2000, the entire contents of which are hereby incorporated by reference.

FIELD OF THE INVENTION

This invention pertains to an improvement in the treatment of vascular disorders and in the treatment of atherosclerosis in particular. More specifically, the invention is directed to the mucosal administration of heat shock protein peptides and biologically active fragments or analogs of such heat shock protein peptides for the prevention and therapeutic treatment of vascular disorders. The invention also includes aerosol, oral, and enteral formulations of heat shock protein peptides useful in the treatment of vascular disorders in mammals.

BACKGROUND OF THE INVENTION

Atherosclerosis, a multifactorial process resulting in thickening of the intimal layer of arterial vessels, is characterized by an accumulation of lipids within the vessel wall and accompanying mononuclear cell infiltration and smooth muscle cell proliferation. It is a leading cause of mortality and morbidity due to cardiovascular and cerebrovascular disease in the western world. The initial lesion of atherosclerosis is the fatty streak, the focal collection of lipoprotein particles within the intima.

The current treatments for the prevention and treatment of atherosclerosis include certain pharmacological approaches, in addition to alteration of lifestyle factors which can ameliorate atherosclerosis, such as diet control, weight loss, increased exercise, and smoking cessation. Examples of pharmacological agents in current use for the treatment and prevention of atherosclerosis are hydroxymnethylglutaryl-coenzyrne A (HMGCoA) reductase inhibitors (statins) to control high LDL, nicotinic acid to control high lipoprotein (a) and low high density lipoprotein (HDL), and fibric acid derivatives to control high levels of triglycerides. Adjunctive pharmacological treatment includes measures directed toward control of diabetes mellitus and hypertension.

In view of the foregoing, a need still exists to develop methods and compositions for treating and/or preventing vascular disorders such as atherosclerosis. Preferably, such methods and compositions would include non-invasive modes of administration and, more preferably, be based, in part, on the molecular interactions which mediate an inflammatory response.

SUMMARY OF THE INVENTION

The invention solves these and other problems by providing methods and compositions for treating vascular disorders, including atherosclerosis.

It has been unexpectedly discovered by the present inventors that mucosal administration of a heat shock protein peptide, for example mycobacterial heat shock protein 65 (HSP65), is an effective treatment for vascular disorders, such as atherosclerosis. In one aspect, the invention is directed to a method for treating vascular disorders in a mammal in need of such treatment, comprising orally (or more generally, mucosally) administering to the mammal an effective amount of an agent comprising a heat-shock protein ("HSP"), and/or therapeutically effective fragments or analogs of a heat shock protein. Preferably, the administration is continued for a period of time sufficient to achieve at least one of the following:

(i) reduction in the level of proinflammatory Th1 cytokines;

(ii) increase in the level of anti-inflammatory Th2 cytokines; or (iii) amelioration, retardation or suppression of at least one clinical or histological symptom of a vascular disorder.

Although not wishing to be bound to any particular theory or mechanism, it is believed that mucosally administered HSPs according to the invention can initiate immunological responses in a subject which prevent, retard or arrest an inflammatory response associated with a vascular disorder. For ease of discussion, the invention is described in terms of administering a heat shock protein; however, it is to be understood that therapeutically effective fragments or analogs of HSPs can be used in addition to or in place of HSPs to practice the claimed invention.

The present invention also relates to formulations adapted for mucosal administration, and/or delivery systems adapted from mucosal administration, comprising a HSP and useful in the treatment of vascular disorders.

It has now been discovered that an improved and more effective method for preventing or treating vascular disorders in mammals comprises mucosal administration of one or more heat shock protein peptides. Heat shock proteins (HSPs) are well known in the art and are discussed in detail below. Therapeutically effective fragments and analogs of HSPs can be identified in screening assays which measure, e.g., any one or more of the above-listed parameters. Exemplary animal models for selecting therapeutically effective HSPs, fragments and analogs thereof, are provided in the Examples.

Thus, according to one aspect of the invention, a method for treating (including preventing) a vascular disorder in a mammal is provided The method involves administering to a mucosal surface of the mammal at least one agent selected from the group consisting of a heat shock protein, a therapeutically effective fragment of a heat shock protein, and a therapeutically effective analog of a heat shock protein, wherein the agent is present in an effective amount for treating the disorder. In certain embodiments, the vascular disorder is an inflammatory vascular disorder and the effective amount is an amount sufficient to suppress, in whole or in part, the inflanmmatory response.

According to one embodiment of this aspect of the invention, the mucosal surface an includes nasal epithelium. In a second embodiment the mucosal surface includes oral mucosa. In yet other embodiments the mucosal surface includes a luminal surface of a gastrointestinal organ selected from the group consisting of: stomach, small intestine, large intestine, and rectum. In certain embodiments of this aspect of the invention, the disorder includes a cell-mediated immune response. In certain other embodiments, the disorder includes an antibody-mediated immune response. In a preferred embodiment of this aspect of the invention, the disorder is atherosclerosis. In another preferred embodiment of this aspect of the invention, the heat shock protein is mycobacterial HSP65. In another preferred embodiment of this aspect of the invention, the beat shock protein is human HSP60. In yet another preferred embodiment of this aspect of the invention, the heat shock protein is chlamydial HSP60.

In a second aspect, the present invention provides a method for treating a vascular disorder (e.g., an inflammatory vascular disorder) in a mammal. The method includes administering to the mammal by inhalation an effective amount of a composition containing at least one agent selected from the group consisting of a heat shock protein, a therapeutically effective fragment of a heat shock protein, and a therapeutically effective analog of a heat shock protein, wherein the agent is present in an effective amount for treating the disorder. In certain embodiments, the vascular disorder is an inflammatory vascular disorder and the effective amount is an amount sufficient to suppress, in whole or in part, the inflammatory response.

In certain embodiments of this aspect of the invention, the disorder includes a cell-mediated immune response. In certain other embodiments, the disorder includes an antibody-mediated immune response. In a preferred embodiment of this aspect of the invention, the disorder is atherosclerosis. In another preferred embodiment of this aspect of the invention, the heat shock protein is mycobacterial HSP65. In another preferred embodiment of this aspect of the invention, the heat shock protein is human HSP60. In yet another preferred embodiment of this aspect of the invention, the heat shock protein is chlamydial HSP60. In yet another preferred embodiment of this aspect of the invention, the agent is in aerosol form.

In a third aspect, the present invention provides a method for suppressing a vascular disorder in a mammal, which includes administering to the mammal via the pulmonary tract an effective amount of a composition comprising at least one member selected from the group consisting of a heat shock protein, a therapeutically effective fragment of a heat shock protein, and a therapeutically effective analog of a heat shock protein, wherein the agent is present in an effective amount for treating the disorder. In certain embodiments, the vascular disorder is an inflammatory vascular disorder and the effective amount is an amount sufficient to suppress, in whole or in part, the inflammatory response. In a preferred embodiment of this aspect of the invention, the disorder is atherosclerosis. In another preferred embodiment of this aspect of the invention, the heat shock protein is mycobacterial HSP65. In another preferred embodiment of this aspect of the invention, the heat shock protein is human HSP60. In yet another preferred embodiment of this aspect of the to invention, the heat shock protein is chlamydial HSP60. In yet another preferred embodiment of this aspect of the invention, the agent is in aerosol form.

The invention provides in yet another aspect a method for treating a vascular disorder in a mammal, which includes orally or enterally administering to the mammal an effective amount of a composition containing at least one agent selected from the group consisting of a heat shock protein, a therapeutically effective fragment of the heat shock protein, and a therapeutically effective analog of the heat shock protein, wherein the agent is present in an effective amount for treating the disorder. In certain embodiments, the vascular disorder is an inflammatory vascular disorder and the effective amount is an amount sufficient to suppress, in whole or in part, the inflammatory response.

In certain embodiments of this aspect of the invention, the disorder includes a cell-mediated immune response. In certain other embodiments, the disorder includes an antibody-mediated immune response. In a preferred embodiment of this aspect of the invention, the disorder is atherosclerosis. In another preferred embodiment of this aspect of the invention, the heat shock protein is mycobacterial HSP65. In another preferred embodiment of this aspect of the invention, the heat shock protein is human HSP60. In yet another preferred embodiment of this aspect of the invention, the heat shock protein is chlamydial HSP60. According to one embodiment of this aspect of the invention, the composition is administered orally. According to another embodiment of this aspect of the invention, the composition is administered enterally. In certain embodiments the composition is administered in solid form. In certain other embodiments the composition is administered in semi-solid form. In yet other embodiments the composition is administered in liquid form. In other embodiments the administered composition further includes a pharmaceutically acceptable carrier.

In yet another aspect the present invention provides a composition for treating a vascular disorder in a mammal, which includes at least one agent selected from the group consisting of a heat shock protein, a therapeutically effective fragment of the heat shock protein, and a therapeutically effective analog of the heat shock protein, wherein the agent is present in an effective amount for treating the disorder. In certain embodiments, the vascular disorder is an inflammatory vascular disorder and the effective amount is an amount sufficient to suppress, in whole or in part, the inflammatory response.

In certain embodiments of this aspect of the invention, the disorder includes a cell-mediated immune response. In certain other embodiments, the disorder includes an antibody-mediated immune response. In a preferred embodiment of this aspect of the invention, the disorder is atherosclerosis. In another preferred embodiment of this aspect of the invention, the heat shock protein is mycobacterial HSP65. In another preferred embodiment of this aspect of the invention, the heat shock protein is human HSP60. In yet another preferred embodiment of this aspect of the invention, the heat shock protein is chlamydial HSP60. In certain embodiments the composition is administered in solid form. In certain other embodiments the composition is administered in semi-solid form. In yet other embodiments the composition is administered in liquid form. In yet other embodiments the composition is administered in aerosol form. In certain embodiments of this aspect of the invention, the composition further includes a pharmaceutically acceptable carrier.

These and other aspect of the invention, as well as various advantages and utilities, will be more apparent with reference to the detailed description of the preferred embodiments and to the accompanying drawings.

All documents identified in this application are incorporated in their entirety herein by reference.

BRIEF DESCRIPTION OF THE DRAWINGS

FIG. 2 is a pair of graphs showing HSP65-induced secretion of (A) IFN-γ and (B) IL-10 by popliteal lymph node cells from C57BL/6 mice nasally treated with 0.8 µg HSP65 or 0.8 µg OVA peptide prior to immunization with HSP65 in CFA.

Figure 1:
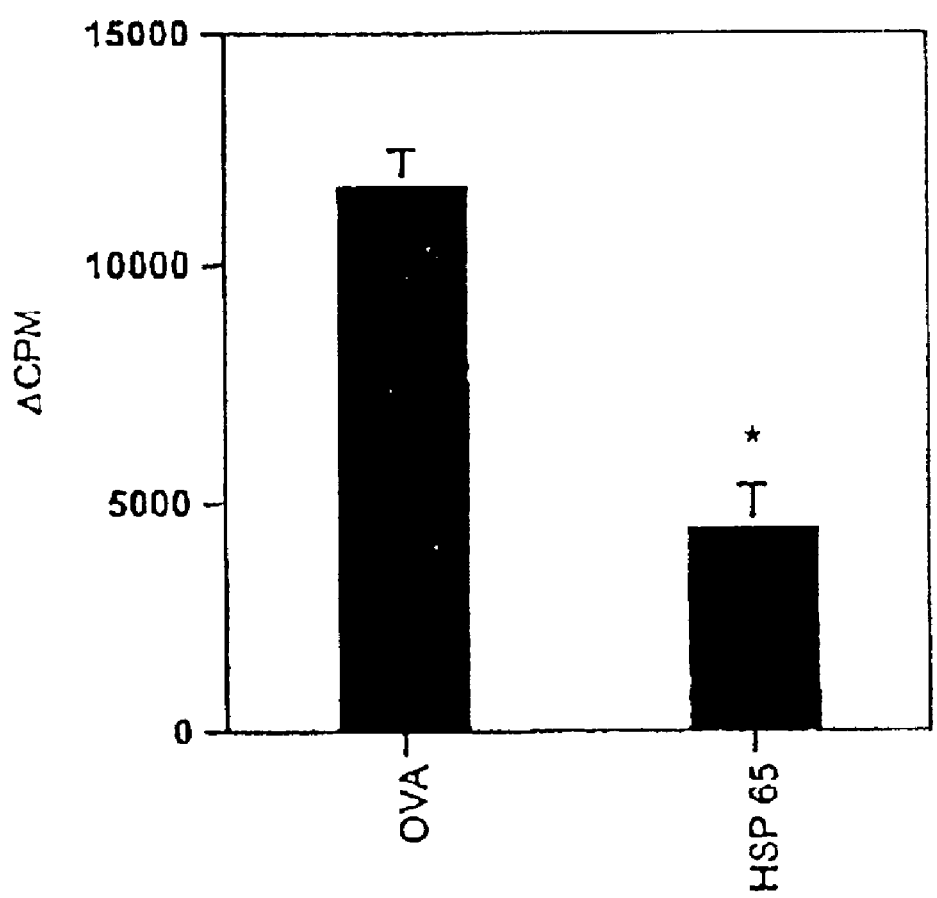
FIG. 1 is a graph showing HSP65-induced proliferation of popliteal lymph node cells from C57BL/6 mice nasally treated with 0.8 µg HSP65 or 0.8 µg ovalbumin (OVA) peptide prior to immunization with HSP65 in complete Freund's adjuvant (CFA).

The figures are illustrative and are not essential to enablement of the inventions disclosed herein.

These and other embodiments of the subject invention will be described in the detailed description.

DETAILED DESCRIPTION OF THE INVENTION

All publications and patent applications listed herein are hereby incorporated by reference.

The following terms as used in this disclosure have the meanings ascribed to them below. "Mammal" is defined herein as any warm-blooded higher vertebrate organism (including a human) having an immune system and being susceptible to vascular disorders or an induced or spontaneous animal model thereof.

"Abatement", "suppression" or "reduction" of an immune response or reaction includes partial reduction or amelioration of one or more symptoms of the attack or reaction, e.g., reduction in number of activated T cells or in number of antibodies or in the levels of at least one proinflammatory cytokine (e.g., interferon (IFN)-γ, interleukin (IL)-2 or tumor necrosis factor (TNF)) or an increase in the levels of at least one anti-inflammatory cytokine, such as transforming growth factor (TGF)-β, IL-4, IL-10.

As employed herein the term "treatment" refers to treatment of an active disorder in an affected individual or to prophylactic administration to prevent a disorder in a susceptible individual. "Treatmnent" of vascular disorders such as atherosclerosis is intended to include, although not be limited to, one or more of the following:

(i) alteration of the profile of one or more cytokines in vascular disorder patient or animal model so that it conforms to or approaches the cytokine profile of a sex-and-age-matched subject without a vascular disorder, (ii) delay in the progress of vascular disorder-related symptoms (detectable by methods known in the art);

(iii) amelioration of the vascular disorder as evaluated by one or more of the symptoms, factors and criteria as in (ii) of this definition, or by observation by a physician specializing in vascular disorders, or (iv) decrease in the amount of vascular inflammation compared to the amount that would otherwise have been observed absent the treatment. Accordingly, treatment includes (a) delaying or preventing onset of clinical symptoms of vascular disorder, which is prevention of the clinical symptoms of disorder; (b) abating or arresting, delaying or preventing an abnormal inflammatory response (which may or may not be accompanied by clinical symptoms) which can have the attributes of both therapy (if the occurrence of inflammation precedes the treatment) and prevention (to the extent that inflammation, if unchecked, would later cause clinical symptoms); and (c) treating vascular disorder after the appearance of clinical symptoms, which is therapy. The clinical symptoms referred to above include those recognized by physicians and others skilled in the art and may include those described in, for example, *Harrison's Principles of Internal Medicine*, 14th ed., A S Fauci et al., eds., New York: McGraw-Hill, 1998.

Mucosal tolerance according to the invention is an advantageous method for treating vascular disorders for several reasons:

(1) Absence of toxicity. For example, no toxicity has been observed in clinical trials or animal experiments involving oral or other mucosal administration of other protein antigens, such as bovine myelin (which contains myelin basic protein (MBP) and proteolipid protein (PLP)) to humans afflicted with multiple sclerosis, or oral or by-inhalation administration of chicken Type II collagen to humans or rodents afflicted with rheumatoid arthritis (or a corresponding animal model disorder); or oral administration of bovine S-antigen to humans afflicted with uveoretinitis; or oral administration of insulin to healthy volunteers.

(2) Containment of immunosuppression. Conventional treatments of immune system disorders involve administration of non-specific immunosuppressive agents, such as the cytotoxic drugs methotrexate, cyclophosphamide (CYTOXAN®, Bristol-Myers Squibb), azathioprine (IMURAN®, Glaxo Wellcome) and cyclosporin A (SANDIMMUNE®, NEORAL®, Novartis). Steroid compounds such as prednisone and methylprednisolone (also non-specific immunosuppressants) are also employed in many instances. All of these currently employed drugs have limited efficacy (e.g., against both cell-mediated and antibody-mediated autoimmune disorders). Furthermore, such drugs have significant toxic and other side effects and, more important, eventually induce "global" immunosuppression in the subject being treated. Prolonged treatment with the drugs down-regulates the normal protective immune response against pathogens, thereby increasing the risk of infection. In addition, patients subjected to prolonged global immunosuppression have an increased risk of developing severe medical complications from the treatment such as malignancies, kidney failure and diabetes.

(3) Convenience of therapy. Mucosal administration is more convenient than parenteral, or other forms, of administration.

The present inventors carried out a series of experiments to discover whether mucosal tolerization techniques causes suppression of inflammation characteristic of atherosclerosis. The use of the mucosal route to induce tolerance against an autoimmune response was found effective in an animal model to suppress undesirable immune response associated with atherosclerosis, and to reduce symptoms of the disorder in an animal model. The Examples include a detailed description of these experiments.

The present method of treating vascular disorders, particularly atherosclerosis, is based on the mucosal administration results, in one embodiment, in regulation of the specific immune response thought to be associated with the disorder. While not wishing to be bound by theory, the present inventors believe that suppression of this response is effected primarily by an active suppression mechanism, i.e., the elicitation of T cells characterized by an anti-inflammatory cytolcine profile.

"Mucosal" administration includes oral, enteral, intragastic, nasal, buccal or intrapulmonary administration, and more generally any method of administration (e.g., by inhalation) of an active ingredient that brings the ingredient in contact with the immune system of the treated subject at the mucosa-associated lymphoid tissue (MALT), including that of the gut, nasal, buccal, bronchial or pulmonary mucosa.

In one embodiment, the present invention provides a method for treating a mammal suffering from (or at risk for developing) vascular disorders comprising mucosally administering to the mammal an effective amount of a composition comprising a heat shock protein, a therapeutically effective HSP fragment, and/or a therapeutically effective HSP analog. Administration is preferably continued for a period of time sufficient to achieve a change in one of the parameters described above. In a preferred embodiment, the present invention provides the method as described wherein the mammal is human.

The present invention also provides a pharmaceutical formulation for administering to a mammal suffering from a vascular disorder, comprising an oral or other mucosal dosage form and delivery system containing an effective amount of a heat shock protein, a therapeutically effective HSP fragment, and/or a therapeutically effective HSP analog that is sufficient to achieve at least one of the above-described measures of treatment.

In one embodiment, the present invention provides the above-described pharmaceutical formulation wherein the oral dosage form is a solid dosage form selected from the group consisting of a tablet, a capsule and a caplet. In another embodiment, the present invention provides the pharmaceutical formulation as described above wherein the oral dosage form comprises an aqueous suspension solution of a heat shock protein, a therapeutically effective HSP fragment, and/or a therapeutically effective HSP analog. In additional embodiments, the present invention provides the pharmaceutical formulation as above-described further comprising a pharmaceutically acceptable carrier or diluent.

The present invention also provides a pharmaceutical formulation for administering to a mammal suffering from a vascular disorder comprising a dosage form according to the invention adapted for nasal or buccal administration. In one embodiment, the present invention provides the pharmaceutical formulation in aerosol or spray form to be delivered by inhalation as described above further comprising a pharmaceutically acceptable carrier or diluent. The formulation can, for example, be administered in a nebulizer or inhaler.

Antigens that may be used to Induce Tolerance

It has now been discovered that mucosal administration of heat shock protein peptides (or therapeutically effective fragments or analogs thereof), particularly in aerosol form, is effective in treating atherosclerosis in mammals. A particularly surprising and unexpected development is the discovery that administration of heat shock protein peptides in aerosol form is more effective in preventing and treating atherosclerosis in mammals than administration of the same heat shock protein peptides in solid form via the oral route. Also surprising is the discovery that it is possible to achieve effective suppression and prevention of vascular disorders in mammals using a smaller quantity of such heat shock protein peptides in an aerosol form than by administration of a solid dosage form. The aerosol administration of heat shock protein peptides has been found to be effective in suppressing both cell-mediated and antibody-mediated inflammatory responses associated with atherosclerosis.

The heat shock proteins are a family of approximately twenty-five highly conserved proteins upregulated in response to various forms of stress. Heat shock proteins are among the most highly conserved proteins in existence. Generally HSPs are survival factors, involved in protein folding, assembly of protein complexes, and prevention of protein unfolding. Certain heat shock proteins are also known as chaperonin proteins and as GroE or GroEL proteins. Several reviews of heat shock proteins have been published, including Lindquist S (1986) *Ann Rev Biochem* 55:1151–91; Pelham H R (1986) *Cell* 46:959–61; Lindquist S and Craig E A (1988) *Ann Rev Genet* 22:631–77; Pelham H R (1989) *EMBO J* 8:3171–6; Schlesinger M J (1990) *J Biol Chem* 265:12111–4; Kaufinarm S H (1990) *Immunol Today* 11:129–37; Morimoto R I (1991) *Cancer Cells* 3:295–301; and Nover L (1991) *Nature New Biol* 3:855–9. In recent years it has been reported that HSPs can play important roles in the development of disorders such as rheumatoid arthritis, insulin-dependent diabetes mellitus, and multiple sclerosis.

Heat shock proteins may be obtained from any suitable source, including from bacterial, mycobacterial, vertebrate, mammalian (e.g., human), invertebrate, and plant (including yeast) sources. Preferred categories of heat shock proteins include those derived from mycobacterial, mammalian (e.g., human), and bacterial sources.

As used herein the term "HSP65" refers to a particular 65 kDa isoform of heat shock protein derived from *Mycobacterium tuberculosis*. HSP65 is a 540 amino acid residue protein described in Shinnick T M *J Bacteriol* 169:1080–8 (1987) and GenBank Accession No. A26950. The amino acid sequence for HSP65 is presented as SEQ ID NO: 1.

In certain preferred embodiments peptide fragments of HSP65 are peptides at least 10 amino acids long that occur between amino acid residues 201–300 of HSP65. These HSP65 fragments include, for example, fragments having amino acid residues 201–210, 211–220, 221–230, 231–240, 241–250, 251–260, 261–270, 271–280, 281–290, or 291–300. Also included as HSP65 fragments are fragments having amino acid residues 192–201, 202–211, 212–221, 222–231, 232–241, 242–251, 252–261, 262–271, 272–281, 282–291, or 292–301; fragments having amino acid residues 193–203, 203–212, 213–222, 223–232, 233–242, 243–252, 253–262, 263–272, 273–282, 283–292, or 293–302; and so on, i.e., every 10-mer containing at least one amino acid residue between 201–300.

```
MAKTIAYDEE ARRGLERGLN ALADAVKVTL GPKGRNVVLE KKWGAPTITN DGVSIAKEIE   60 SEQ ID NO:1

LEDPYEKIGA ELVKEVAKKT DDVAGDGTTT ATVLAQALVR EGLRNVAAGA NPLGLKRGIE  120

KAVEKVTETL LKGAKEVETK EQIAATAAIS AGDQSIGDLI AEAMDKVGNE GVITVEESNT  180

FGLQLELTEG MRFDKGYISG YFVTDPERQE AVLEDPYILL VSSKVSTVKD LLPLLEKVIG  240

AGKPLLIIAE DVEGEALSTL VVNKIRGTFK SVAVKAPGFG DRRKAMLQDM AILTGGQVIS  300

EEVGLTLENA DLSLLGKARK VVVTKDETTI VEGAGDTDAI AGRVAQIRQE IENSDSDYDR  360

EKLQERLAKL AGGVAVIKAG AATEVELKER KHRIEDAVRN AKAAVEEGIV AGGGVTLLQA  420

APTLDELKLE GDEATGANIV KVALEAPLKQ IAFNSGLBPG VVAEKVRNLP AGHGLNAQTG  480

VYEDLLAAGV ADPVKVTRSA LQNAASIAGL FLTTEAVVAD KPEKEKASVP GGGDMGGMDF  540
```

The complete sequence structure for this and other heat shock protein peptides are available on the GenBank public database.

As used herein the term "HSP65" also refers to a particular 65 kDa isoform of heat shock protein derived from *Mycobacterium bovis* Bacillus Calmette-Guerin (BCG), as the protein sequence of this HSP65 identical to that of HSP65 derived from *Mycobacterium tuberculosis*. Thole JE et al. *Infect Immun* 55:1466–75 (1987); GenBank Accession No. P06806. HSP65 can further include any polypeptide having the same amino acid sequence as SEQ ID NO:1 as well as polypeptides having a substantial degree of homology to SEQ ID NO:1.

As used herein the term "human HSP60" refers to a particular 60 kDa isoform of heat shock protein derived from humans. Human HSP60 is a 573 amino acid residue protein described in Jindal S et al. *Mol Cell Biol* 9:2279–83 (1989) and GenBank Accession No. AAA60127. The amino acid sequence of HSP60 is presented as SEQ ID NO:2. Human HSP60 can also include any polypeptide with the same amino acid sequence as SEQ ID NO:2 as well as polypeptides having a substantial degree of homology to SEQ ID NO:2. SEQ ID NO:2.

```
MLRLPTVFRQ MRPVSRVLAP HLTRAYAKDV KFGADARALM LQGVDLLADA VAVTMGPKGR   60 SEQ ID NO:2

TVIIEQSWGS PKVTKDGVTV AKSIDLKDKY KNIGAKLVQD VANNTNEEAG DGTTTATVLA  120

RSIAKEGFEK ISKGANPVEI RRGVMLAVDA VIAELKKQSK PVTTPEEIAQ VATISANGDK  180

EIGNIISDAM KKVGRKGVIT VKDGKTLNDE LEIIEGMKFD RGYISPYFIN TSKGQKCEFQ  240

DAYVLLSEKK ISSIQSIVPA LEIANAHRKP LVIIAEDVDG EALSTLVLNR LKVGLQVVAV  300

KAPGFGDNRK NQLKDMAIAT GGAVFGEEGL TLNLEDVQPH DLGKVGEVIV TKDDAMLLKG  360

KGDKAQIEKR IQEIIEQLDV TTSEYEKEKL NERLAKLSDG VAVLKVGGTS DVEVNEKKDR  420

VTDALNATRA AVEEGIVLGG GCALLRCIPA LDSLTPANED QKIGIEIIKR TLKIPAMTIA  480

KNAGVEGSLI VEKIMQSSSE VGYDAMAGDF VNMVEKGIID PTKVVRTALL DAAGVASLLT  540

TAEVVVTEIP KEEKDPGMGA MGGMGGGMGG GMF                              573
```

As used herein the term "chlamydial HSP60" refers to a particular 60 kDa isoform of heat shock protein derived from various species of Chlamydia, including *Chlamydophila pneumoniae*. Chlamydial HSP60 is a 544 amino acid residue protein described in Kikuta LC et al. (1991) *Infect Immun* 59:4665–9, Kalman S et al. (1999) Nat Genet 21:385–9, and GenBank Accession No. AAD18287. The amino acid sequence of chlamydial HSP60 is presented as SEQ ID NO:3. Chlamydial HSP60 can also include any polypeptide with the same amino acid sequence as SEQ ID NO:3 as well as polypeptides having a substantial degree of homology to SEQ ID NO:3, e.g., HSP60 derived form other chlamydia species. Yuan M et al., (1992) Infect Immun 60:2288–96.

```
MAAKNIKYNE EARKKIHKGV KTLAEAVKVT LGPKGRHVVI DKSFGSPQVT KDGVTVAKEI   60 SEQ ID NO:3

ELEDKHENMG AQMVKEVASK TADKAGDGTT TATVLAEAIY SEGLRNVTAG ANPMDLKRGI  120

DKAVKVVVDE LKKISKPVQH HKEIAQVATI SANNDSEIGN LIAEAMEKVG KNGSITVEEA  180

KGFETVLDVV EGMNFNRGYL SSYFSTNPET QECVLEDALI LIYDKKISGI KDFLPVLQQV  240

AESGRPLLII AEEIEGEALA TLVVNRLRAG FRVCAVKAPG FGDRRKAMLE DIAILTGGQL  300

VSEELGMKLE NTTLAMLGKA KKVIVTKEDT TIVEGLGNKP DIQARCDNIK KQIEDSTSDY  360

DKEKLQERLA KLSGGVAVIR VGAATEIEMK EKKDRVDDAQ HATIAAVEEG ILPGGGTALV  420

RCIPTLEAFL PMLANEDEAI GTRIILKALT APLKQIASNA GKEGAIICQQ VLARSANEGY  480

DALRDAYTDM IDAGILDPTK VTRSALESAA SIAGLLLTTE ALIADIPEEK SSSAPAMPSA  540

GMDY                                                              544
```

As used herein the terms "mycobacterial HSP65," "human HSP60," and "chlamydial HSP60" also embrace homologs and alleles of mycobacterial HSP65, human HSP60, and chlamydial HSP60, respectively. In general homologs and alleles typically will share at least 40% nucleotide identity and/or at least 50% amino acid identity to the sequences of specified nucleic acids and polypeptides, respectively. Thus homologs and alleles of mycobacterial HSP65, human HSP60, and chlamydial HSP60 typically will share at least 40% nucleotide identity and/or at least 50% amino acid identity to the sequences of mycobacterial HSP65, human HSP60, and chlamydial HSP60 nucleic acids and polypeptides, respectively. In some instances homologs and alleles will share at least 50% nucleotide identity and/or at least 65% amino acid identity and in still other instances will share at least 60% nucleotide identity and/or at least 75% amino acid identity. Preferably the homologs and alleles will share at least 80% nucleotide identity and/or at least 90% amino acid identity, and more preferably will share at least 90% nucleotide identity and/or at least 95% amino acid identity. Most preferably the homologs and alleles will share at least 95% nucleotide identity and/or at least 99% amino acid identity. The homology can be calculated using various publicly available software tools developed by the National Center for Biotechnology Information (NCBI, Bethesda, Md.) that can be obtained through the internet. Exemplary tools include the BLAST system available from the NCBI, used with default settings. Pairwise and ClustalW alignments (BLOSUM30 matrix setting) as well as Kyte-Doolittle hydropathic analysis can be obtained, for example, using the MacVector sequence analysis software (Oxford Molecular Group). Watson-Crick complements of the foregoing nucleic acids also are embraced by the invention. Nonlimiting examples of HSP homologs are provided in Table 1.

TABLE 1

GenBank accession numbers for exemplary homologs of SEQ ID NO's 1–3

|  | Accession No. | Source | Length |
|---|---|---|---|
| Mycobacterial HSP65 | AAA25354.1 | M. leprae | 588 |
|  | AAA99670.2 | M. avium | 582 |
|  | AAB49990.1 | T. tyrosinosolvens | 539 |
|  | AAF33788.1 | P. acnes | 544 |
|  | AAF91444.1 | M. avium | 541 |
|  | BAB12250.1 | P. granulosum | 533 |

TABLE 1-continued

GenBank accession numbers for exemplary homologs of SEQ ID NO's 1–3

|  | Accession No. | Source | Length |
|---|---|---|---|
|  | CAB93056 | S. coelicolor | 541 |
|  | O33658 | S. lividans | 477 |
|  | P06806 | M. bovis | 540 |
|  | P09239 | M. leprae | 541 |
|  | P42384 | M. paratuberculosis | 541 |
|  | Q00768 | S. albus | 540 |
| Human HSP60 | A34173 | Chinese hamster | 573 |
|  | AAB94640.1 | C. variipennis | 581 |
|  | AAD27589.1 | O. volvulus | 598 |
|  | CAA10230.1 | P. acuminatus | 580 |
|  | CAA37653.1 | mouse | 555 |
|  | CAA37654.1 | rat | 547 |
|  | CAB56199.1 | P. lividus | 582 |
|  | CAB58441 | M. persicae | 573 |
|  | I53052 | human | 573 |
|  | O02649 | D. melanogaster | 573 |
|  | P19226 | mouse | 573 |
|  | P29185 | Z. mays | 577 |
|  | P50140 | C. elegans | 568 |
|  | S13089 | rat | 573 |
| Chlamydial HSP60 | A60273 | C. trachomatis | 544 |
|  | AAA19871 | C. muridarum | 544 |
|  | AAA23128 | C. trachomatis | 544 |
|  | AAA97911 | C. muridarum | 544 |
|  | AAD18287 | C. pneumoniae | 544 |
|  | AAD18915 | C. pneumoniae | 526 |
|  | AAD19036 | C. pneumoniae | 519 |
|  | AAD26143 | C. pecorum | 497 |
|  | AAD26144 | C. abortus | 497 |
|  | AAD26145 | C. pneumoniae | 497 |

TABLE 1-continued

GenBank accession numbers for
exemplary homologs of SEQ ID NO's 1–3

| Accession No. | Source | Length |
|---|---|---|
| B41479 | C. trachomatis | 544 |
| BAA98985 | C. pneumoniae | 526 |
| BAA99106 | C. pneumoniae | 519 |
| CAA42673 | C. pneumoniae | 544 |
| D72036 | C. pneumoniae | 526 |
| I40731 | C. trachomatis | 544 |
| P15599 | C. psittaci | 544 |
| P17203 | C. trachomatis | 544 |
| P31681 | C. pneumoniae | 544 |
| Q59322 | C. muridarum | 544 |
| S19023 | C. pneumoniae | 544 |

The invention also embraces variants of the preferred HSP protein peptides described above. As used herein, a "variant" of a protein peptide is a polypeptide which contains one or more modifications to the primary amino acid sequence of a protein peptide. Accordingly, a "variant" of an HSP protein peptide is a polypeptide which contains one or more modifications to the primary amino acid sequence of an HSP protein peptide. Modifications which create an HSP variant can be made to an HSP protein peptide for a variety of reasons, including 1) to reduce or eliminate an activity of an HSP protein peptide; 2) to enhance a property of an HSP protein peptide; 3) to provide a novel activity or property to an HSP protein peptide; or 4) to establish that an amino acid substitution docs or does not affect HSP protein peptide activity. Modifications to an HSP protein peptide are typically made to the nucleic acid which encodes the HSP protein peptide, and can include deletions, point mutations, truncations, amino acid substitutions and additions of amino acids or non-amino acid moieties. Alternatively, modifications can be made directly to the protein peptide, such as by cleavage, addition of a linker molecule, addition of a detectable moiety (for example, biotin, fluorophore, radioisotope, enzyme, or peptide), addition of a fatty acid, and the like.

Modifications also embrace fusion proteins comprising all or part of the HSP amino acid sequence. One of skill in the art will be familiar with methods for predicting the effect on protein conformation of a change in protein sequence, and can thus "design" a variant HSP according to known methods. One example of such a method is described by Dahiyat and Mayo in *Science* 278:82–87 (1997), whereby proteins can be designed de novo. The method can be applied to a known protein to vary a only a portion of the polypeptide sequence. By applying the computational methods of Dahiyat and Mayo, specific variants of an HSP protein peptide can be proposed and tested to determine whether the variant retains a desired conformation.

Variants include HSP protein peptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of an HSP protein peptide by eliminating proteolysis by proteases in an expression system (e.g., dibasic amino acid residues in yeast expression systems in which KEX2 protease activity is present).

Mutations of a nucleic acid which encode an HSP protein peptide preferably preserve the amino acid reading frame of the coding sequence, and preferably do not create regions in the nucleic acid which are likely to hybridize to form secondary structures, such as hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with a desired property. Further mutations can be made to variants (or to non-variant HSP protein peptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of an HSP gene or cDNA clone to enhance expression of the polypeptide.

The activity of variants of HSP protein peptides can be tested by cloning the gene encoding the variant HSP protein peptide into a prokaryotic or eukaryotic (e.g., mammalian) expression vector, introducing the vector into an appropriate host cell, expressing the variant HSP protein peptide, and testing for a functional capability of the HSP protein peptides as disclosed herein. For example, the variant HSP protein peptide can be tested for its ability to suppress a vascular disorder, as set forth below in the examples.

The skilled artisan will also realize that conservative amino acid substitutions may be made in HSP protein peptides to provide functionally equivalent variants of the foregoing polypeptides, i.e., variants which retain the functional capabilities of the HSP protein peptides. As used herein, a "conservative amino acid substitution" refers to an amino acid substitution which does not alter the relative charge or size characteristics of the polypeptide in which the amino acid substitution is made. Variants can be prepared according to methods for altering polypeptide sequence known to one of ordinary skill in the art such as are found in references which compile such methods, e.g., *Molecular Cloning. A Laboratory Manual*, J. Sambrook, et al., eds., Second Edition, Cold Spring Harbor Laboratory Press, Cold Spring Harbor, N.Y., 1989, or *Current Protocols in Molecular Biology*, F M Ausubel, et al., eds., John Wiley & Sons, Inc., New York. Exemplary functionally equivalent variants of the HSP protein peptides include polypeptides having conservative amino acid substitutions of SEQ ID NOs:1–3. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

HSPs useful in the practice of the invention can be obtained through any method known in the art. HSP65, human HSP60, and chlamydial HSP60 can be obtained from a variety of commercial sources, prepared from natural sources using conventional protein preparatory methods, or expressed as recombinant proteins. Purified HSP65 can be obtained from commercial sources such as StressGen Biotechnologies Corporation, Vancouver, BC, Canada. Purified recombinant human HSP60 can be obtained from commercial sources such as StressGen Biotechnologies Corporation, Vancouver, BC, Canada.

In preferred embodiments the HSP is isolated. As used herein with reference to an HSP, the term "isolated" means removed from its natural biological surroundings, i.e., from the cells in which they occur in nature. An isolated HSP can but need not necessarily be purified. In preferred embodiments the HSP peptide fragments and HSP peptide analogs are isolated. As used herein with reference to HSP peptide fragments and HSP peptide analogs, the term "isolated" means removed from its natural biological surroundings or biological materials. For example, if the HSP peptide fragments or HSP analogs are prepared by recombinant cloning techniques, the HSP peptide fragments or HSP analogs are separated from the cells used to express them. Isolated HSP peptide fragments or HSP analogs can but need not necessarily be purified.

HSP fragments useful according to the invention are preferably immunogenic and can be derived from the HSPs through any method known in the art. For example, the fragments can be prepared as synthetic oligopeptides as described further herein. The HSP peptide fragments will typically be at least 10 amino acids long, and may be at least 15, 16, 17, 18, 19, 20 or more consecutive amino acids in length. HSP peptide fragments can include any HSP-specific peptide at least one residue shorter than the corresponding full-length HSP.

Formulations for Mucosal Administration

Admninistration of more than one antigen is possible, and may be desirable (e.g., when the patient's immune T cells recognize more than one antigen).

Suitable formulations according to the invention include formulations adapted for oral, enteral, buccal, nasal, bronchial or intrapulmonary administration. The preparation of such formulations is well within the skill of the art. It is preferred that such formulations not contain substances that can act as adjuvants in order to avoid sensitization of the treated subject. It is also preferred that the antigens employed be of synthetic provenance and not isolated from biological sources to avoid the risk of infection (notably, but not exclusively, to avoid transmission of agent responsible for the Creutzfeld-Jacob disease). Additionally, it is preferred that the formulation not contain adsorption promoting agents or ingredients that protect against proteolytic degradation.

Suitable oral formulations for use in tolerization of T-cell mediated immune responses according to the present invention can be in any suitable orally administrable form, for example, a pill, a liquid, or a capsule or caplet containing an effective amount of antigen. Each oral formulation may additionally comprise inert constituents including pharmaceutically acceptable carriers, diluents, fillers, disintegrants, flavorings, stabilizers, preservatives, solubilizing or emulsifying agents and salts as is well-known in the art. For example, tablets may be formulated in accordance with conventional procedures employing solid carriers and other excipients well-known in the art. Capsules may be made from any is 1 cellulose derivatives. Nonlimiting examples of solid carriers include starch, sugar, bentonite, silica and other commonly used inert ingredients. Diluents for liquid oral formulations can include inter alia saline, syrup, dextrose and water.

The antigens (i.e., HSPs and therapeutically effective fragments and analogs thereof) used in the present invention can also be made up in liquid formulations or dosage forms such as, for example, suspensions or solutions in a physiologically acceptable aqueous liquid medium. Such liquid media include water, or suitable beverages, such as fruit juice or tea which will be convenient for the patient to sip at spaced apart intervals throughout the day. When given orally in liquid formulations the antigen may be dissolved or suspended in a physiologically acceptable liquid medium, and for this purpose the antigen may be solubilized by manipulation of its molecule (e.g., hydrolysis, partial hydrolysis or trypsinization) or adjustment of the pH within physiologically acceptable limits (e.g., 3.5 to 8). Alternatively, the antigen may be reduced to micronized form and suspended in a physiologically acceptable liquid medium, or in a solution.

Sustained release oral delivery systems are also contemplated and are preferred. Nonlimiting examples of sustained release oral dosage forms include those descnied in U.S. Pat. No. 4,704,295, issued Nov. 3, 1987; U.S. Pat. No. 4,556,552, issued Dec. 3, 1985; U.S. Pat. No. 4,309,404, issued Jan. 5, 1982; U.S. Pat. No. 4,309,406, issued Jan. 5, 1982; U.S. Pat. No. 5,405,619, issued Apr. 10, 1995; PCT International Application WO 85/02092, published May 23, 1985; U.S. Pat. No. 5,416,071, issued May 16, 1995; U.S. Pat. No. 5,371,109, issued Dec. 6, 1994; U.S. Pat. No. 5,356,635, issued Oct. 18, 1994; U.S. Pat. No. 5,236,704, issued Aug. 17, 1993; U.S. Pat. No. 5,151,272, issued Sep. 29, 1992; U.S. Pat. No. 4,985,253, issued Jan. 15, 1991; U.S. Pat. No. 4,895,724, issued Jan. 23, 1990; and U.S. Pat. No. 4,675,189, issued Jun. 23, 1987.

Sustained release oral dosage forms coated with bioadhesives can also be used. Examples are compositions disclosed in European Published Application EP 516141; U.S. Pat. No. 4,226,848; U.S. Pat. No. 4,713,243; U.S. Pat. No. 4,940,587; PCT International Application WO 85/02092; European Published Application 205282; Smart J D et al. (1984) *J Pharm Pharmacol* 36:295–9; Sala et al. (1989) *Proceed Intern Symp Control Rel Bioact Mater* 16:420–1; Hunter et al. (1983) *International Journal of Pharmaceutics* 17:59–64; "Bioadhesion—Possibilities and Future Trends, Kellaway," Course No. 470, May 22–24, 1989.

Commercially available sustained release formulations and devices include those marketed by ALZA Corporation, Palo Alto, Calif., under tradename ALZET, INFUSET, IVOS, OROS, OSMET, or described in one or more U.S. Pat. No. 5,284,660, issued Feb. 9, 1994; U.S. Pat. No. 5,141,750, issued Aug. 25, 1992; U.S. Pat. No. 5,110,597, issued May 5, 1992; U.S. Pat. No. 4,917,895, issued Apr. 17, 1990; U.S. Pat. No. 4,837,027, issued Jun. 6, 1989; U.S. Pat. No. 3,993,073, issued Nov. 23, 1976; U.S. Pat. No. 3,948,262, issued Apr. 6, 1976; U.S. Pat. No. 3,944,064, issued Mar. 16, 1976; and U.S. Pat. No. 3,699,963; International Applications PCT/US93/10077 and PCT/US93/11660; and European Published Applications EP 259013 and EP 354742.

Sustained release compositions and devices are suitable for use in the present invention because they serve to prolong contact between the antigen and the gut-associated lymphoid tissue (GALT) and thus prolong contact between the antigen and the immune system. In addition, sustained release compositions obviate the need for discrete multi-dose administration of the antigen and permit the required amount of antigen to be delivered to GALT in one or two daily doses. This is anticipated to improve patient compliance.

Orally administrable pharmaceutical formulations containing one or more of a heat shock protein, a therapeutically effective HSP fragment, and/or a therapeutically effective HSP analog are prepared and administered to mammals who have manifested symptoms of vascular disorder, such as atherosclerosis. Additionally, subjects who are at risk for developing a vascular disorder, i.e., have a genetic predisposition to developing the disorder, as determined through suitable means, such as genetic studies and analysis, are treated with similar oral preparations.

Pharmaceutical formulations for oral or enteral administration to treat vascular disorders are prepared from a heat shock protein, a therapeutically effective HSP fragment, and/or a therapeutically effective HSP analog and a pharmaceutically acceptable carrier suitable for oral ingestion. The quantity of a heat shock protein, a therapeutically effective HSP fragment, and/or a therapeutically effective HSP analog in each daily dose may be between 0.01 mg and 1000 mg per day. However, the total dose required for treatment can vary according to the individual and the severity of the condition. This amount can be further refined by well-known methods such as establishing a matrix of dosages and frequencies of administration.

For by-inhalation administration (i.e., delivery to the bronchopulmonary mucosa) suitable sprays and aerosols can be used, for example using a nebulizer such as those described in U.S. Pat. No. 4,624,251 issued Nov. 25, 1986; U.S. Pat. No. 3,703,173 issued Nov. 21, 1972; U.S. Pat. No. 3,561,444 issued Feb. 9, 1971; and U.S. Pat. No. 4,635,627 issued Jan. 13, 1971. The aerosol material is inhaled by the subject to be treated.

Other systems of aerosol delivery, such as the pressurized metered dose inhaler (MDI) and the dry powder inhaler as disclosed in Newman S P in Aerosols and the Lung, S W Clarke S W and D Davis, eds. pp. 197–224, Butterworths, London, England, 1984, can be used when practicing the present invention.

Aerosol delivery systems of the type disclosed herein are available from numerous commercial sources including Fisons Corporation (Bedford, Mass.), Schering Corp. (Kenilworth, N.J.) and American Pharmoseal Co. (Valencia, Calif.).

Formulations for nasal administration can be administered as a dry powder or in an aqueous solution. Preferred aerosol pharmaceutical formulations may comprise for example, a physiologically acceptable buffered saline solution containing a heat shock protein, a therapeutically effective HSP fragment, and/or a therapeutically effective HSP analog of the present invention.

Dry aerosol in the form of finely divided solid comprising a heat shock protein, a therapeutically effective HSP fragment, and/or a therapeutically effective HSP analog in particle form, which particles are not dissolved or suspended in a liquid are useful in the practice of the present invention. The antigen may be in the form of dusting powders and comprise finely divided particles having an average particle size of between about 1 and 5 $\mu$m, preferably between 2 and 3 $\mu$m. Finely divided antigen particles may be prepared by pulverization and screen filtration using techniques well known in the art. The particles may be administered by inhaling a predetermined quantity of the finely divided material, which can be in the form of a powder.

Specific non-limiting examples of the carriers and/or diluents that are useful in the pharmaceutical formulations of the present invention include water and physiologically acceptable buffered saline solutions such as phosphate buffered saline solutions pH 7.0–8.0.

The nasally administered formulation of the present invention may include a thermosetting gel which increases in viscosity at body temperature upon contact with the 10 nasal mucosa Formulations for buccal administration can include mucoadhesive mixed with effective amounts of a heat shock protein, a therapeutically effective HSP fragment, and/or a therapeutically effective HSP analog. Effective amounts are anticipated to vary according to the formulation employed. For formulation administered by inhalation, the effective amount is likely to be less than that of the oral dose.

Preferably, the duration of treatment in humans should be a minimum of two weeks, and typically three months, and may be continued indefinitely or as long as benefits persist. The treatment may be discontinued if desired (in the judgment of the attending physician) and the patient monitored for signs of relapse. If clinical symptoms or other disorder indicators show that the patient is relapsing, treatment may resume.

As will be understood by those skilled in the art, the dosage will vary with the antigen administered and may vary with the sex, age, and physical condition of the patient as well as with other concurrent treatments being administered. Consequently, adjustment and refinement of the dosages used and the administration schedules will preferably be determined based on these factors and especially on the patient's response to the treatment. Such determinations, however, require no more than routine experimentation, as illustrated in Examples provided below.

Administration of a heat shock protein, a therapeutically effective HSP fragment, and/or a therapeutically effective HSP analog can be conjoined with mucosal administration of one or more enhancers, i.e. substances that enhance the tolerizing effect of the a heat shock protein, a therapeutically effective HSP fragment, and/or a therapeutically effective HSP analog antigen. Such enhancers include lipopolysaccharide (LPS), Lipid A (as described in U.S. application Ser. No. 08/202,677, published as WO 91/01333), IL-4, IL-10 and Type I interferon (See, e.g., U.S. application Ser. Nos. 08/420,980 and 08/420,979 and WO 95/27499 and WO 95/27500). As used in the preceding sentence, "conjoined with" means before, substantially simultaneously with, or after administration of these antigens. Naturally, administration of the conjoined substance should not precede nor follow administration of the antigen by so long an interval of time that the relevant effects of the substance administered first have worn off. Therefore, enhancers should usually be administered within about 24 hours before or after the a heat shock protein, a therapeutically effective HSP fragment, and/or a therapeutically effective HSP analog antigen and preferably within about one hour.

As used herein the term "therapeutically effective fragment" refers to a peptide or polypeptide containing partial amino acid sequences or moieties of heat shock proteins possessing the ability to treat a vascular disorder. Preferably, such fragments are able to suppress or prevent an inflammatory response upon mucosal administration. Such fragments need not possess the inflammatory properties of the entire heat shock protein. By way of non-limiting example, when MBP is administered parenterally to susceptible mice in the presence of an adjuvant, it induces experimental allergic encephalomyelitis RAE). It is known that certain non-disease-inducing fragments of MBP (i.e., fragments of MBP which do not induce EAE when administered parenterally with an adjuvant) nevertheless possess autoimmune-suppressive activity when administered orally (or enterally) or in aerosol form to mammals suffering from EAE. Examples of such fragments are reported in U.S. patent application Ser. No. 07/065,734, filed Jun. 24, 1987, and International Patent Application No. PCT/US88/02139, filed Jun. 24, 1988. Therapeutically effective fragments and analogs can be identified by observing a change in cytokine release profile, such as illustrated in the Examples or in other in vitro or in vivo assays which are predictive of a human vascular disorder and from which agents can be selected which alleviate detectable symptoms of the disorder. Cytokines can be measured using routine assays, including commercially available immunoassays such as radioimmunoassay (RIA) and enzyme-linked immunosorbent assay (ELISA).

As employed herein the term "therapeutically effective analogs" of such heat shock proteins or fragments thereof refer to compounds that are structurally related to these heat shock protein peptides or to their therapeutically effective fragments (e.g., inflammatory response-suppressive fragments) and which possess the same biological activity, i.e., the ability to treat the condition, e.g., by eliminating or suppressing the inflammatory response, upon mucosal administration, either nasally, orally, or enterally. By way of non-limiting example, the term includes peptides having amino acid sequences which differ from the amino acid sequence of the heat shock protein peptide or therapeutically effective fragments thereof by one or more amino acid residues (while still retaining the inflammatory response-suppressive activity of the heat shock protein peptide or fragment) as well as compounds or compositions which mimic the inflammatory response-suppressive activity of the heat shock protein peptide in its ability to suppress or alleviate the symptoms of the disorder.

Fragments and analogs of heat shock protein peptides for use in the present invention can be synthesized using solid phase synthesis techniques well known in the art such as those of Merrifield R B (1962) *Fed Proc Am Soc Exp Biol* 21:412 and *J Am Chem Soc* 85:2149 (1963), and Mitchel A R et al. as well as Tam J et al. (1976) *J Am Chem Soc* 98:7357. Analogs can be constructed by identifying an equivalent amino acid sequence and using the peptide synthesis techniques disclosed above. Therapeutically effective analogs and fragments can also be obtained using recombinant DNA techniques well known in the art.

As used herein the term "inflanmmatory disease-suppressive agent" is a category of a therapeutically effective agent which refers to a compound or composition which can be administered to a mucosal surface of a mammal to suppress, prevent or delay the clinical onset or manifestation of an inflammatory vascular disease. The term includes heat shock protein peptides that are active against a specific inflammatory vascular disorder, as well as inflammatory disease-suppressive fragments or analogs thereof as defined above.

As used herein the term "vascular disorder" refers to a disease or process involving tissue intrinsic to the blood vessels, particularly the arterial vessels, in which the lumen of affected vessels are narrowed as a result. The archetype of vascular disorder is atherosclerosis. A vascular disorder can involve vessels associated with one or more vascular beds, e.g., the coronary arteries, the cerebral arteries, the aorta, the renal arteries, the splanchnic bed, the peripheral arteries, etc. Included are arterial aneurysms, e.g., aortic aneurysm. Such aneurysms are preferably non-traumatic in origin and can but need not necessarily be atherosclerotic. Also included are a number of principally inflammatory vascular disorders, including but not limited to: allergic angiitis and granulomatosis (Churg-Strauss disease), Behget's syndrome, Cogan's syndrome, graft-versus-host disease (GvHD), Henoch-Schönlein purpura, Kawaski disease, leukocytoclastic vasculitis, polyarteritis nodosa (PAN), microscopic polyangiitis, polyangiitis overlap syndrome, Takayasu's arteritis, temporal arteritis, transplant rejection, Wegener's granulomatosis, and thromboangiitis obliterans (Buerger's disease). The measurable symptoms and diagnostic markers of these vascular disorders are well established in the literature and known to physicians practicing in this field. See, for example, *Harrison's Principles of Internal Medicine*, 14th ed., A S Fauci et al., eds., New York: McGraw-Hill, 1998.

The tolerance induced by the autoimmune-suppressive agents of this invention is dose-dependent Dose dependency was also seen in the autoimmune arthritis system. Moreover, the mucosal administration of an irrelevant antigen (i.e., one not implicated in an autoimmune disease, such as ovalbumin (OVA) peptide, histone protein, or certain synthetic fragments of MBP) has no effect on the clinical manifestation of the autoimmune disease.

Administration of heat shock proteins via the aerosol route for the treatment of immune disorder has several advantages over other routes of administration. Ease of administration is one important advantage. Also, as shown below in Example 3, aerosol administration of HSP65 is effective in treating atherosclerosis at substantially lower doses than those required to treat this disorder when the same agent was administered orally via the oral route in a solid dosage form. A further advantage is that the aerosol administration route involves less exposure of the heat shock protein peptides of the present invention to degradative gastric juices, which may act to reduce the efficacy of such agents.

It should be noted that the amount of inflammatory response-suppressive agent of the present invention which the treated animal receives via aerosol administration is substantially lower than the total amount of the agent which is administered. It is believed that only 1/200 of the total dosage present in the nebulizer is actually taken up on the pulmonary surface of the treated animals. The majority of the autoimmune suppressive agent nebulized into the cages is not inhaled by the animals but non-specifically adheres to the cages and to the animals. Therefore, aerosol administration is much more effective than oral or enteral administration where in the latter case all of the autoimmune suppressive agent is delivered to the treated animals.

Various animal models have been developed for the study of atherosclerosis and are predictive of human atherosclerosis. Among the more common models are those in which inbred strains of mice have been rendered deficient for either the LDL receptor (LDLR −/−) or apolipoprotein E (apo E −/−) by a gene knockout. The LDL receptor is a 160 kDa glycoprotein responsible for the transfer of LDL out of the plasma and into the cytoplasm of virtually all cell types. The major site of LDL uptake and catabolism is the liver. LDLR −/− mice created on a C57BL/6 background develop accelerated atherosclerosis when fed a high cholesterol diet, but not when fed a regular chow diet. By contrast, wild-type C57BL/6 mice typically do not develop accelerated atherosclerosis on either a high cholesterol or a regular chow diet.

In one very recent study Afek and coworkers found that LDLR −/− C57BL/6 mice immunized subcutaneously with 10 or 100 $\mu$g of heat-killed Mycobacterium tuberculosis and maintained on a normal chow diet for three months developed significantly larger fatty streaks than negative control mice immunized with bovine serum albumin. Afek A et al. (2000) *J Autoimmun* 14:115–121. These and other animal models can be used to select HSPs that are useful in accordance with the methods of the invention.

The invention is further described below by reference to examples, the purpose of which is to illustrate the present invention without limiting its scope. All documents cited herein are incorporated by reference.

EXAMPLES

Experimental Methods

Animals. Wild-type C57BL/6 and LDLR −/− C57BL/6 mice (6 –8 weeks of age) were obtained from the Jackson Laboratory, Bar Harbor, Me., and used in all experiments.

HSP65. Purified *Mycobacterium bovis* BCG HSP65 was obtained from StressGen Biotechnologies Corporation, Victoria, BC, Canada.

Nasal Administration. The aerosol HSP65 was administered in phosphate buffered saline (PBS, pH 7.4) using a nebulizer. Aerosol was administered to test animals through a hole punched in the side of the cage which held the animals. For aerosolization, a nebulizer (American Pharmoseal Co., Valencia, Calif., Catalog No. 002038) was attached to an air pressure outlet delivering the equivalent of 7.4 liters of oxygen (the amount of oxygen used in a hospital for nebulization). The nebulizer produced droplets of spray having a diameter of between about 0.3 micrometers and about 0.5 micrometers in diameter. 25 mg of HSP65 was dissolved in 5 ml of PBS. This was then aerosolized over a 10 to 15 minute period to 5 mice per cage (having dimensions 14"×12"×7", for height, width and depth, respectively). During aerosolization, a fine mist was created in the cage and the mice moved about freely.

Oral Administration. Heat shock proteins and OVA peptides were orally administered in a 1 ml volume through a syringe fitted with 18G ball-point needle according to the schedules specified in the examples below.

Cell Proliferation Assays. At the specified time, mice were sacrificed and their spleens and popliteal lymph nodes were removed. A single-cell suspension was prepared by pressing the spleens or lymph nodes through a stainless steel mesh. After being washed twice, the cells were resuspended in RPMI 1640 containing 1% glutamine, 1% penicillin/streptomycin, 1% non-essential amino acids, 5% fetal calf serum and $5\times10^{-5}$ M 2-mercaptoethanol. The cells were then seeded into a 96-well flat-bottom plate in quadruplicate at a concentration of $2.5\times10^{-5}$ cells/well and cultured with various concentrations of HSP65 at 37° C. with 5% $CO_2$ for 72 hours. Tritiated thymidine was then added to the culture at 1 $\mu$Ci/well. The cells were harvested on an automatic cell harvester 6 hours after the pulsing and proliferation was determined by [$^3$H]-thymidine incorporation as measured by liquid scintillation counting.

Cytokine ELISAs. A solid-phase enzyme-linked immunoabsorbent assay (ELISA) was used for determination of concentrations of various cytokines. Microtiter plates were coated with anti-cytokine antibodies (100 ng/well) in 0.1 ml of 0.IM sodium bicarbonate, pH 8.2. Plates were incubated for 18 hrs at 25° C. After 3 washes with PBS/Tween-20 (Bio-Rad), pH 7.5, plates were incubated with 3% bovine serum albumin (BSA)/PBS for 2 hrs at 37° C., washed twice, and 100 $\mu$l of diluted serum was added in quadruplicate. The plates were incubated for 2 hrs at 37° C. After three rinses with PBS/Tween-20, plates were incubated with 100 $\mu$l/well of peroxidase-conjugated goat anti-rat IgG antibody (Tago, U.S.A.) diluted 1:1000 in 1% BSA/PBS for 1 hr at 25° C. Color reaction was obtained by exposure to D-phenylenediamine (0.4 mg/ml phosphate/citrate buffer, pH 5.0) containing 30% hydrogen peroxide. The reaction was stopped by adding 0.4N $H_2SO_4$ and OD 492 nm was read on an ELISA reader.

Plaque Area Mesurements. Quantification of atherosclerotic fatty streak lesions was performed by calculation of lesion size in the aortic arch as previously described. Qiao JH et al. (1994) *Arterioscler Thromb* 14:1480–97. In brief, the heart and upper portion of the aorta were perfused with PBS, removerd from the animals, and the peripheral fat was carefully removed. The aortic arch section was embebded in optimal cutting temperature (OCT) medium and snap frozen. Every other 10 $\mu$m thick section throughout the aortic arch was stained with oil red O and taken for analysis. An observer blinded to the treatment counted lesion areas on a calibrated grid. The total area was reported in $\mu m^2$.

Immunohistochemistry. Immunohistochemistry staining with antibodies to mouse Mac-3 and mouse CD4 (PharMingen, San Diego, Calif.) was performed using 5 $\mu$m cryostat sections of the aortic arch as previously described. Qiao J H et al. (1994) *Arterioscler Thromb* 14:1480–97. Briefly, cryostat sections were air-dried, fixed in acetone, and stained as appropriate with MAC-3 for macrophages, anti-CD4 for T cells, anti-IL-10 (BD PharMingen, San Diego, Calif.), anti-IFN-γ, or anti-TGF-β (R&D Systems, Minneapolis, Minn.). Areas that stained positive for macrophages were measured using computer-assisted image quantification (IPLAB Spectrum P 3.1). Lymphocytes identified by anti-CD4 or anti-cytokine antibody staining were counted microscopically by four blinded observers. Results were reported as cells stained/total cells×100 % as scored above.

Diets. Where indicated, mice were fed a high cholesterol diet (Research Diets; 1.25% cholesterol, 0 % cholate) or a conventional mouse diet (chow).

Statistical Analysis. Data are presented as mean±SEM. Statistical differences were determined by 1-way ANOVA. $P<0.05$ was accepted as statistically significant.

Example 1

Nasal pretreatment with HSP65 leads to a suppressed immune response in vitro upon subsequent exposure to HSP65.

Wild-type C57BL/6 mice were treated nasally three times over a week with 0.8 $\mu$g HSP65; 8 $\mu$g HSP65, or equal amounts of OVA peptide. Three days after the last nasal treatment, mice were immunized subcutaneously with 8 $\mu$g HSP65 in conjunction with either CFA (equivalent to 50 $\mu$g of *Mycobacterium tuberculosis*) or IFA. All mice were maintained on normal chow diets. Tissues were harvested ten days after immunization for use in the in vitro cell proliferation and cytolcine assays discussed below.

Cell proliferation assays. Single-cell suspensions from popliteal lymph nodes draining the immunization site were prepared in complete medium and aliquoted into individual wells supplemented with log-fold dilutions of HSP65 to final concentrations ranging from 10 $\mu$g/ml to 0.01 $\mu$g/ml. Cell proliferation was measured in a $^3$H-thymridine uptake assay following conventional methods. All measurements were performed in triplicate. Background counts from cells in wells receiving no HSP65 were subtracted from all. Results from this assay are shown in FIG. 1. As evident from the data presented in FIG. 1, popliteal cells taken from control mice nasally pretreated with 0.8 $\mu$g OVA peptide and immunized with HSP65 in CFA responded vigorously upon challenge with HSP65 at a concentration of 10 $\mu$g/ml. In contrast, popliteal cells taken from mice nasally pretreated with 0.8 $\mu$g HSP65 and immunized with HSP65 in CFA exhibited a greatly attenuated proliferative response to HSP65 at a concentration of 10 $\mu$g/ml (=0.003 for OVA+CFA versus HSP+CFA). Popliteal cells from mice nasally pretreated with 0.8 $\mu$g HSP65 and immunized with HSP65 in IFA proliferated less than half as much as the controls. Proliferative responses to HSP65 introduced at lower concentrations yielded too few counts to make comparisons.

The same assay was also performed using splenocytes, with a similar pattern of findings. Spleen cells taken from control mice nasally pretreated with 0.8 $\mu$g OVA peptide and then immunized with HSP65 in CFA responded vigorously upon challenge with HSP65 at a concentration of 10 $\mu$g/ml.

In contrast, spleen cells taken from mice nasally pretreated with 0.8 µg HSP65 and then immunized with HSP65 in CFA, and likewise spleen cells from mice nasally pretreated with 0.8 µg HSP65 and then immunized with HSP65 in IFA, proliferated about half as much as the controls. Proliferative responses to HSP65 introduced at lower concentrations yielded too few counts to make comparisons.

Interestingly, despite the immunosuppressive effect of nasally pretreating with 0.8 µg HSP65, nasal pretreatment with a ten-fold higher dose of HSP65 (8 µg) appeared to be immunizing. Proliferation data using popliteal lymph node cells in the presence of HSP65 at 10 µg/ml, as above, revealed that cells taken from mice pretreated with 8 µg HSP65 and then immunized with HSP65 in CFA, and cells taken from mice similarly pretreated but then immunized with HSP65 in IFA, both exhibited greater proliferation in response to HSP65 at 10 µg/ml than controls. Thus, nasal pretreatment with the lower dose of HSP65 tended to tolerize, while pretreatment with the higher dose tended to immunize, with respect to HSP65.

Cytokine secretion assays. Single-cell suspensions from popliteal lymph nodes draining the immunization site were prepared in complete medium and aliquoted into individual wells supplemented with HSP65 at a final concentration of 10 µg/ml. After 24 hours of incubation, tissue culture supernatants were prepared by centrifugation and filtration (0.4 µm) for use in ELISAs. Samples were serially diluted in buffer and run in triplicate on ELISA plates with internal standard curve positive and negative controls, following instructions provided by the manufacturer. Static colorimetric measurements were performed using a multiwell plate reader set to the proper wavelength. The different assays measured interferon gamma (IFN-γ), interleukin 6 (IL-6), IL-10, and transforming growth factor beta (TGF-β). Results are shown in FIG. 2.

FIG. 2A depicts the results of IFN-γ ELISA for popliteal lymph node cells taken from mice nasally pretreated with 0.8 µg OVA peptide or HSP65 and subsequently immunized with HSP65 in CFA. Compared to control pretreatment with OVA peptide and subsequent immunization with HSP65 in CFA, IFN-γ was greatly reduced (p=0.01) in popliteal cells taken from mice pretreated with 0.8 µg HSP65. In contrast, IFN-γ was increased compared to controls in popliteal cells taken from mice pretreated with 8 µg HSP65 and subsequently immunized with HSP65 in IFA IL-6 was likewise reduced in popliteal cells taken from mice pretreated with 0.8 µg HSP65 and subsequently immunized with HSP65 in IFA or CFA, compared to cells taken from control pretreated mice. Nasal pretreatment with 8 µg HSP65 and subsequent immunization with HSP65 in IFA completely suppressed IL6 secretion in this assay, while similar pretreatment combined with subsequent immunization with HSP65 in CFA had little to no suppressive effect.

FIG. 2B depicts the results of IL-10 ELISA for popliteal lymph node cells taken from mice nasally pretreated with 0.8 µg HSP65 and subsequently immunized with HSP65 in CFA. Compared to control pretreatment with OVA peptide and subsequent immunization with HSP65 in CFA, IL-10 was significantly increased (p=0.04) in popliteal cells taken from mice pretreated with 0.8 jig HSP65 and subsequently immunized with HSP65 in CFA. IL-10 secretion by popliteal cells from mice pretreated with 8 µg HSP65 was not significantly different from controls.

Secretion of TGF-µ by popliteal cells taken from mice nasally pretreated with HSP65 and immunized with HSP65 in IFA was increased compared to controls. Substitution of CFA for IFA led to the opposite result, i.e., TGF-β secretion by these cells was reduced compared to controls.

Similar experiments were also performed using splenocytes. IFN-γ ELISA was performed for spleen cells taken from mice nasally pretreated with 0.8 µg HSP65 or 8 µg HSP65 and subsequently immunized with HSP65 in CFA or HSP65 in IFA. Compared to control pretreatment with OVA peptide and subsequent immunization with HSP65 in CFA, IFN-γ was greatly reduced in spleen cells taken from mice pretreated with 0.8 µg or 8 µg HSP65 and subsequently immunized with HSP65 in IFA. In contrast, IFN-γ was unchanged or increased compared to controls in spleen cells taken from mice pretreated with 0.8 µg or 8 µg HSP65 and subsequently immunized with HSP65 in CFA.

Secretion of TGF-β by spleen cells taken from mice nasally pretreated with HSP65 and immunized with HSP65 in CFA was essentially abolished compared to controls. Substitution of IFA for CFA led to the result that TGF-β secretion by these cells was increased or unchanged compared to controls.

Taken as a whole, data from experiments in this example demonstrate that nasal pretreatment with HSP65 leads to a suppressed immune response upon subsequent exposure to HSP65, with possible contributions from reduced proinflammatory cytokine release and increased anti-inflammatory cytokine release.

Example 2

Oral pretreatment with HSP65 leads to a suppressed immune response in vitro upon subsequent exposure to HSP65.

Wild-type C57BL/6 mice were treated orally five times over a week with 8 µg HSP65 or equal amounts of OVA peptide. Three days after the last nasal treatment, mice were immunized subcutaneously with 8 µg HSP65 in either CFA (equivalent to 50 µg of *Mycobacterium tuberculosis*) or IFA. All mice were maintained on normal chow diets. Tissues were harvested ten days after immunization for use in the in vitro cell proliferation and cytokine assays performed as described in Example 1 and discussed below.

Figure 3:
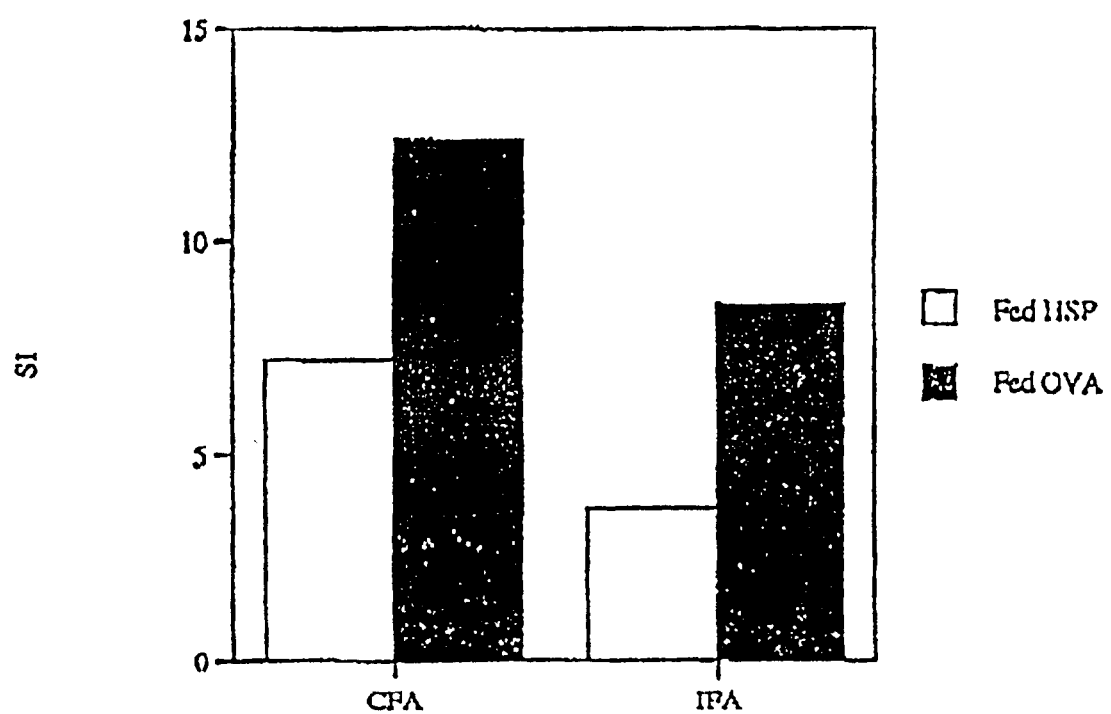
FIG. 3 is a graph showing HSP65-induced proliferation of popliteal lymph node cells from C57BL/6 mice orally treated (fed) with 8 µg of HSP65 or OVA peptide prior to immunization with HSP65 in incomplete Freund's adjuvant (IFA) or CFA.

Cell proliferation assay. As shown in FIG. 3, popliteal lymph node cells from wild-type C57BL/6 mice fed HSP65 (open bars) and subsequently immunized with HSP65 in CFA or IFA proliferated only about half as much as corresponding cells from mice fed OVA peptide (solid bars) and subsequently immunized with HSP65 in CFA or IFA.

Figure 4:
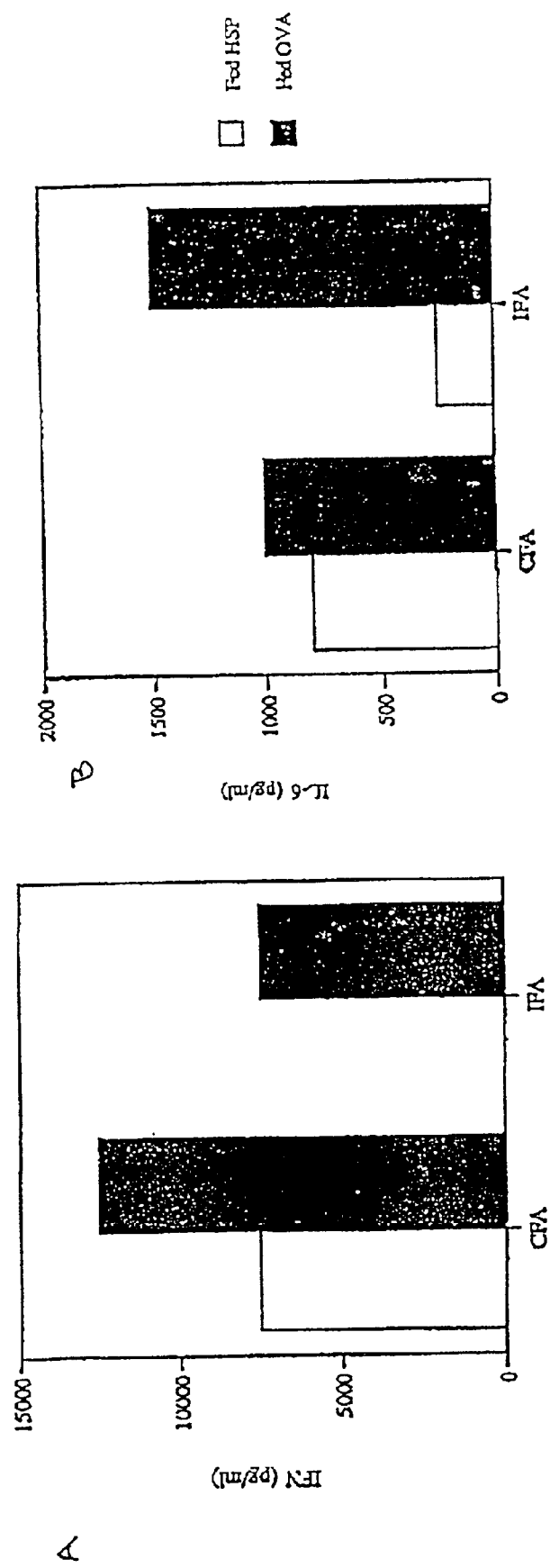
FIG. 4 is a pair of graphs showing the HSP65-induced secretion of (A) IFN-γ and (B) IL-6 by popliteal lymph node cells from C57BL/6 mice orally treated (fed) with 8 µg of HSP65 or OVA peptide prior to inmunization with HSP65 in IFA or CFA.

Cytokine secretion assays. Experiments measuring IFN-γ, IL-6, and IL-10 were performed, using ELISAs as in Example 1, with popliteal lymph node cells taken from mice fed HSP65 or OVA peptide and subsequently immunized with HSP65 in CFA or IFA. As shown in FIG. 4A, IFN-γ secretion was strikingly reduced for cells taken from mice fed HSP65 and subsequently immunized with HSP65 in IFA or with HSP65 in CFA. As shown in FIG. 4B, secretion of IL-6 was also reduced for cells taken from mice fed HSP65 and subsequently immunized with HSP65 in IFA or CFA. IL-10 secretion was minimally affected by feeding of HSP65 in this experimental protocol.

Taken as a whole, data from experiments in this example demonstrate that oral pretreatment with HSP65 leads to a suppressed immune response in vitro upon subsequent exposure to HSP65, in association with reduced proinflammatory cytokine release.

Example 3

HSP65 treatment reduces atherosclerosis and inflammation in the aortic arch of atherosclerosis-prone LRLR −/− mice treated maintained on a high cholesterol diet.

C57BL/6 mice genetically deficient for LDL receptor (LDLR -/- mice) were divided into three groups: a control group nasally treated with OVA peptide, a group nasally treated with 0.8 μg HSP65 three times over one week, and a group orally treated (fed) 8 μg HSP65 five times over one week. A fourth group had untreated wild-type C57BL/6 mice. Control and HSP65-pretreated mice were then placed and maintained on a high cholesterol diet (HCD) for up to 14 weeks. While on the HCD, nasally pretreated mice were nasally retreated once weekly with 0.8 μg HSP65 or OVA, and orally pretreated mice were refed once weekly with 8 μg HSP65. There was no immunization in this experiment. Aortic arches and spleens were taken at 8, 12, and 14 weeks after initiation of the HCD for immunohistochemical analysis and in vitro cell proliferation assays.

Figure 5:
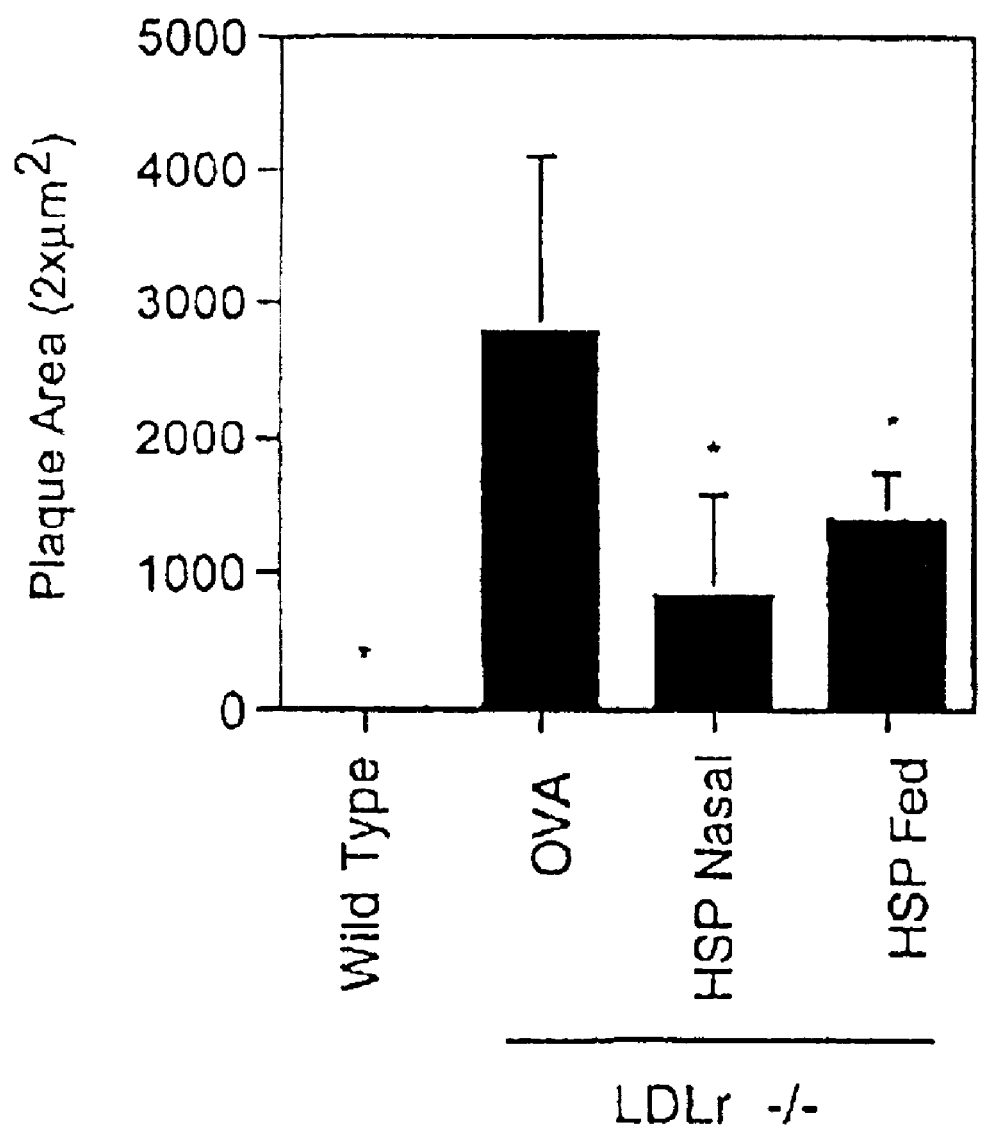
FIG. 5 is a graph showing the aortic arch plaque size ($\mu m^2$) after 8 weeks on a high cholesterol diet in wild-type C57BL/6mice and in low density lipoprotein receptor knockout (LDLr -/-) C57BL/6 mice nasally treated with OVA peptide (OVA), nasally treated with HSP65 (HSP Nasal), or orally treated with HSP65 (HSP Fed). Data represent mean± standard deviation values (n=8), and asterisks (*) denote p<0.05 determined by Student's T-test vs. OVA treated.

Plaque size. Plaque size was significantly reduced in aortic arches of atherosclerosis-prone LDLR -/- mice maintained on a high cholesterol diet following nasal or oral exposure to HSP65. FIG. 5 depicts aortic arch plaque areas (in μm2) 8 weeks after initiation of HCD. As shown in FIG. 5, untreated wild-type C57BL/6 mice developed no plaques after 8 weeks on the HCD, while all LDLR -/- mice developed plaques. However, as shown in FIG. 5, plaques in both the nasally pretreated HSP65 group and the orally pretreated (fed) HSP65 group were significantly smaller than the plaques in the nasally treated OVA group. Plaque size in the nasally pretreated group was smaller than in the orally pretreated group at eight weeks. Plaque size increased in all LDLR -/- mice between 8 and 12 weeks, but the same pattern and significant differences of plaque size were observed.

Figure 6:
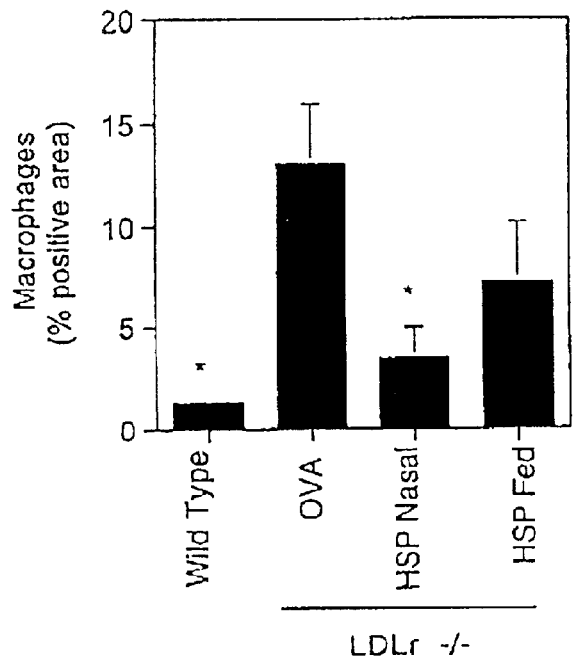
FIG. 6 is a graph showing the percent aortic arch area stained with anti-Mac-3 antibodies after 8 weeks on a high cholesterol diet in wild-type C57BL/6 mice and in LDLR -/- C57BL/6 mice nasally treated with OVA peptide, nasally treated with HSP65, and orally treated with HSP65.

Aortic arch macrophages. Immunohistochemical staining for macrophages was significantly reduced in aortic arches of atherosclerosis-prone LDLR -/- mice maintained on a high cholesterol diet following nasal or oral exposure to HSP65. FIG. 6 depicts the percent aortic arch area stained with Mac-3 antibodies 8 weeks after initiation of HCD. As shown in FIG. 6, untreated wild-type C57BL/6 mice had very low level staining, about 1 percent, after 8 weeks on the HCD. All LDLR -/- mice had increased levels of Mac-3 staining at 8 weeks compared to untreated wild-type C57BL/6 mice, with OVA peptide-treated mice having the greatest level at about 12.5 percent. As shown in FIG. 6, both the nasally pretreated HSP group and the orally pretreated (fed) HSP group had reduced Mac-3 staining compared to the OVA peptide-treated group. Macrophage staining in the nasally pretreated group was about half that in the orally pretreated group, which in turn was about half that in the OVA peptide-treated group at eight weeks. Staining with Mac-3 increased in all LDLR -/- mice between 8 and 12 weeks, but the same pattern and significant differences of staining were observed.

Aortic arch cytokine expression. It is known that in association with the cellular infiltrates, the intima of atherosclerotic plaques express increased amounts of IFN-γ. Aortic arches of atherosclerosis-prone LDLR -/- mice maintained on a high cholesterol diet for 8 weeks following nasal exposure to HSP65 were analyzed by immunohistochemnistry for IFN-γ, IL-10, and TGF-β. Scoring by four blinded observers was based on a scale ranging from 0 (no staining) to 3 (maximal staining) for each cytokine. Results are shown in Table 2. Animals treated with HSP65 had less IFN-γ and increased expression of IL-10 as compared to OVA treated mice. TGF-β levels were similar between groups.

TABLE 2

Cytokine staining in aortic arches of LDL receptor-deficient mice nasally treated with HSP65 and maintained for 8 weeks on high cholesterol diet

| Cytokine | NASAL OVA | | NASAL HSP | | |
|---|---|---|---|---|---|
| | No. Positive | Score | No. Positive | Score | |
| IFN-γ | 5/8 | 1.20 | 1/8 | 0.30 | P = 0.04 |
| IL-10 | 1/8 | 1.50 | 8/8 | 2.20 | P < 0.02 |
| TGF-β | 4/7 | 0.60 | 3/8 | 0.60 | NS |

NS, not significant

Figure 7:
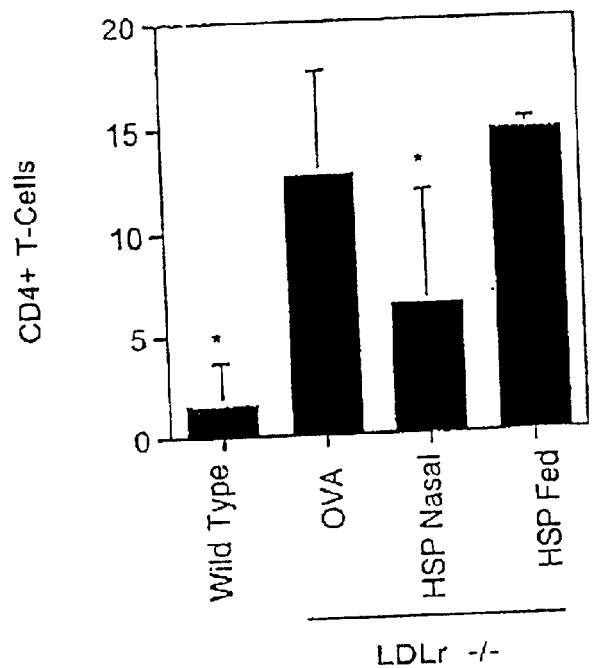
FIG. 7 is a graph showing the percent aortic arch area stained with anti-CD4 antibodies after 8 weeks on a high cholesterol diet in wild-type C57BL/6 mice and in LDLR -/- C57BL/6 mice nasally treated with OVA peptide, nasally treated with HSP65, and orally treated with HSP65.

Aortic arch CD4+T lymphocytes. CD4+T lymphocyte staining was significantly reduced in aortic arches of atherosclerosis-prone LDLR -/- mice maintained on a high cholesterol diet following nasal exposure to HSP65. FIG. 7 depicts the percent aortic arch area stained with anti-CD4 antibodies 8 weeks after initiation of HCD. As shown in FIG. 7, untreated wild-type C57BL/6 mice had very low level staining, about 1 percent, after 8 weeks on the HCD. All LDLR -/- mice had increased levels of CD4 staining at 8 weeks compared to untreated wild-type C57BL/6 mice, with OVA peptide-treated mice having a level at about 12.5 percent As shown in FIG. 7, the nasally pretreated HSP group, but not the orally pretreated (fed) HSP group, had reduced CD4 staining compared to the OVA peptide-treated group. CD4 staining in the nasally pretreated HSP group was about half that in the OVA peptide-treated and orally pretreated HSP groups at eight weeks. Staining for CD4 increased in all LDLR -/- mice between 8 and 12 weeks, with the same pattern and significant differences of staining observed.

Spleen cell proliferation assay. Proliferative response to HSP65 was significantly reduced in spleen cells taken from atherosclerosis-prone LDLR -/- mice maintained on a high cholesterol diet following nasal or oral exposure to HSP65. Spleen cell proliferation assays were performed similarly to those described in Example 1, using spleen cells taken from untreated, nasally pretreated, and orally pretreated LDLR -/- mice after 8, 12, and 14 weeks on HCD. The proliferative response to HSP65 was markedly attenuated for splenocytes taken from the nasally and orally pretreated mice at 14 weeks. Proliferation was reduced to very low levels for splenocytes taken from the nasally and orally pretreated mice at 12 weeks. Data for 12 weeks is presented in Table 2.

Cytokine secretion assays. IFN-γ production was significantly reduced (P=0.01) in spleen cells taken from atherosclerosis-prone LDLR -/- mice maintained for 12 weeks on a high cholesterol diet following nasal exposure to HSP65 (25±5 pg/ml), compared to LDLR -/- mice maintained for 12 weeks on a high cholesterol diet following nasal exposure to OVA peptide (170±20 pg/ml). IL-10 was not detectable in spleen cells from either HSP- or OVA-exposed mice. Data is presented in Table 3.

TABLE 3

Aortic arch staining and in vitro immunologic analysis in LDL receptor-deficient mice nasally treated with HSP65 and maintained on high cholesterol diet for 12 weeks

| | NASAL OVA | NASAL HSP | |
|---|---|---|---|
| Aortic Arch Staining | | | |
| Plaque Area ($2 \times \mu m^2$) | 8926 ± 4060 | 4400 ± 2643 | P = 0.025 |
| Macrophage (% Mac-3+) | 20.2 ± 5.9 | 12.9 ± 6.4 | P = 0.032 |
| T-Cells (# CD4+ cells) | 35.0 ± 7.4 | 22.3 ± 7.5 | P = 0.004 |
| IFN-γ (score) | 1.30 ± 0.53 | 1.25 ± 0.52 | NS |
| IL-10 (score) | 1.25 ± 0.65 | 2.20 ± 0.65 | P = 0.012 |
| TGF-β (score) | 0.95 ± 0.82 | 1.15 ± 0.83 | NS |
| Immune Response (splenocytes) | | | |
| Proliferation (Δ cpm) | 3671 ± 400 | 1679 ± 200 | P = 0.00015 |
| IFN-γ (pg/ml) | 170 ± 20 | 25 ± 5 | P = 0.01 |
| IL-10 (pg/ml) | ND | ND | NA |

NA, not applicable; ND, not detected; NS, not significant

Anti-HSP65 antibody titers and isotypes. LDLR −/− mice maintained for 12 weeks on a high cholesterol diet and mucosally treated with ovalbumin or HSP65 were bled at the end of the experiment, and total IgG, IgG1 and IgG2a were measured by ELISA. Mice nasally treated with HSP65 had significantly lower titers of total IgG and higher values of IgG1 as compared to control treated mice (p=0.05). Mice either nasally or orally treated with HSP65 had decreased titers of IgG2a, however only the orally treated mice had a significant decrease compared to control treated mice (P<0.01). Statistical significance was determined by Student's T test Taken as a whole, data from experiments in this example demonstrate that HSP65 treatment reduces atherosclerosis and inflammation in the aortic arch of atherosclerosis-prone LDLR −/− mice treated maintained on a high cholesterol diet.

---

We claim:

1. A method for treating a vascular disorder in a mammal, which comprises administering to a mucosal surface of said mammal an effective amount of a composition comprising at least one agent selected from the group consisting of an isolated HSP60 heat shock protein, an isolated HSP65 heat shock protein, a therapeutically effective fragment of an isolated HSP60 heat shock protein, and a therapeutically effective fragment of an isolated HSP65 heat shock protein, to treat the vascular disorder.

2. The method of claim 1 wherein said mucosal surface comprises nasal epithelium.

3. The method of claim 1 wherein said mucosal surface comprises oral mucosa.

4. The method of claim 1 wherein said mucosal surface comprises a luminal surface of a gastrointestinal organ selected from the group consisting of: stomach, small intestine, large intestine, and rectum.

5. The method of claim 1 wherein said vascular disorder comprises a cell-mediated immune response.

6. The method of claim 1 wherein said vascular disorder comprises an antibody-mediated immune response.

7. The method of claim 1 wherein said vascular disorder is atherosclerosis.

8. The method of claim 1 wherein said agent is HSP65.

9. The method of claim 1 wherein said agent is human HSP60.

10. The method of claim 1 wherein said agent is chlamydial HSP60.

11. A method for treating a vascular disorder in a mammal, which comprises administering to said mammal by inhalation an effective amount of a composition comprising at least one agent selected from the group consisting of an isolated HSP60 heat shock protein, an isolated HSP65 heat shock protein, a therapeutically effective fragment of an isolated HSP60 heat shock protein, and a therapeutically effective fragment of an isolated HSP65 heat shock protein, to treat the vascular disorder.

12. A method for suppressing a vascular disorder in a mammal, which comprises administering to said mammal via the pulmonary tract an effective amount of at least one agent selected from the group consisting of an isolated HSP60 heat shock protein, an isolated HSP65 heat shock protein, a therapeutically effective fragment of an isolated HSP60 heat shock protein, and a therapeutically effective fragment of an isolated HSP65 heat shock protein, to treat the vascular disorder.

13. A method for treating a vascular disorder in a mammal, which comprises orally or enterally administering to said mammal an effective amount of a composition comprising at least one agent selected from the group consisting of an isolated HSP60 heat shock protein, an isolated HSP65 heat shock protein, a therapeutically effective fragment of an isolated HSP60 heat shock protein, and a therapeutically effective fragment of an isolated HSP65 heat shock protein, to treat the vascular disorder.

* * * * *